US011445692B2

(12) United States Patent
Gar et al.

(10) Patent No.: US 11,445,692 B2
(45) Date of Patent: *Sep. 20, 2022

(54) QUANTITATIVE TRAIT LOCI (QTL) ASSOCIATED WITH SHATTER RESISTANT CAPSULES IN SESAME AND USES THEREOF

(71) Applicant: EQUI-NOM LTD., Kibbutz Givat Brenner (IL)

(72) Inventors: Oron Gar, Kibbutz Sde Yoav (IL); Arie Zackay, Jerusalem (IL); Gil Shalev, Ramot Meir (IL)

(73) Assignee: EQUI-NOM LTD., Kibbutz Givat Brenner (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/706,752

(22) Filed: Dec. 8, 2019

(65) Prior Publication Data

US 2020/0093087 A1    Mar. 26, 2020

Related U.S. Application Data

(63) Continuation-in-part of application No. 16/109,346, filed on Aug. 22, 2018, now Pat. No. 10,577,623, which is a continuation of application No. PCT/IL2018/050520, filed on May 14, 2018.

(60) Provisional application No. 62/506,397, filed on May 15, 2017.

(51) Int. Cl.
*C12Q 1/68* (2018.01)
*A01H 6/66* (2018.01)
*C12Q 1/6895* (2018.01)
*A01H 1/04* (2006.01)

(52) U.S. Cl.
CPC .............. *A01H 6/66* (2018.05); *A01H 1/04* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS

| 4,683,202 | A | 7/1987 | Mullis |
| 5,426,039 | A | 6/1995 | Wallace et al. |
| 5,468,613 | A | 11/1995 | Erlich et al. |
| 5,492,547 | A | 2/1996 | Johnson |
| 5,565,350 | A | 10/1996 | Kmiec |
| 5,981,832 | A | 11/1999 | Johnson |
| 6,100,452 | A | 8/2000 | Langham |
| 6,455,758 | B1 | 9/2002 | Johnson |
| 6,670,524 | B1 | 12/2003 | Potter et al. |
| 7,250,552 | B2 | 7/2007 | Han et al. |
| 7,847,149 | B2 | 12/2010 | Langham |
| 8,058,503 | B1 | 11/2011 | Langham |
| 8,080,707 | B2 * | 12/2011 | Langham .................. A01H 6/66 800/298 |
| 8,581,028 | B2 | 11/2013 | Langham |
| 8,637,729 | B2 | 1/2014 | Foncelle et al. |
| 8,656,692 | B2 | 2/2014 | Langham |
| 8,664,472 | B2 | 3/2014 | Langham |
| 8,692,064 | B2 | 4/2014 | Nguyen et al. |
| 8,779,233 | B1 | 7/2014 | Schnable et al. |
| 8,987,549 | B2 | 3/2015 | Baxter et al. |
| 8,993,835 | B2 | 3/2015 | Langham |
| 9,000,258 | B2 | 4/2015 | Lightart et al. |
| 9,125,372 | B1 | 9/2015 | Langham |
| 9,144,220 | B1 * | 9/2015 | Langham .................. A01H 5/10 |
| 9,167,795 | B2 | 10/2015 | Langham |
| 9,462,820 | B2 | 10/2016 | Tadaki |
| 9,485,936 | B2 | 11/2016 | Page |
| 10,577,623 | B2 * | 3/2020 | Gar ...................... C12Q 1/6895 |
| 11,044,884 | B1 | 6/2021 | Zemach et al. |
| 2003/0208798 | A1 | 11/2003 | Langham |
| 2009/0235394 | A1 | 9/2009 | Langham |
| 2011/0154528 | A1 | 6/2011 | Ragot et al. |
| 2011/0271360 | A1 | 11/2011 | Langham |
| 2014/0215657 | A1 | 7/2014 | Nguyen et al. |
| 2015/0082476 | A1 | 3/2015 | Baxter et al. |
| 2015/0101073 | A1 | 4/2015 | Brugmans et al. |
| 2015/0150155 | A1 | 5/2015 | Black et al. |
| 2017/0055481 | A1 | 3/2017 | Brugmans et al. |
| 2020/0093087 | A1 | 3/2020 | Gar et al. |

(Continued)

FOREIGN PATENT DOCUMENTS

| CN | 106337086 B | 6/2017 |
| IL | 239702 | 6/2015 |
| WO | WO 1993/022443 | 11/1993 |

(Continued)

OTHER PUBLICATIONS

Zhang et al. Genome Biology (2013), 14:401.*
Uzun et al. Plant Breeding (2003)122:95-97.*
Wei et al. BMC Genomics (2011), 12:451.*
Ashri A. & Singh R.J "Chromosome Engineering and Crop Improvement" Sesame (*Seamum indicum* L.) Genetic Resources Oilseed Crops, 4, 2007, pp. 231-280.
Singh et al. "Unlocking the Potential of Genetic Resources for Improvement of Sesame (*Sesamum indicum* L.): The Current Scenario" Gene Pool Diversity and Crop Improvement: vol. 1, Chapter 15, Feb. 2016, pp. 447-479.

(Continued)

*Primary Examiner* — Medina A Ibrahim
(74) *Attorney, Agent, or Firm* — Pearl Cohen Zedek Latzer Baratz LLP

(57) ABSTRACT

The invention relates to sesame genetics and breeding. Specifically, the invention relates to genetic improvement for shatter resistant capsules. More specifically, the invention relates to novel quantitative trait loci (QTL) conferring shatter resistant capsules, and methods thereof, including methods for introgressing the novel QTL into elite germplasm in a breeding program for shatter resistant capsules.

17 Claims, 1 Drawing Sheet
Specification includes a Sequence Listing.

(56) References Cited

U.S. PATENT DOCUMENTS

| | | |
|---|---|---|
| 2021/0307285 A1 | 10/2021 | Tollman |
| 2022/0010325 A1 | 1/2022 | Gar |

FOREIGN PATENT DOCUMENTS

| | | |
|---|---|---|
| WO | WO 2017/103928 | 6/2017 |
| WO | WO 2018/211496 A1 | 11/2018 |
| WO | WO 2020/093065 | 5/2020 |
| WO | WO 2020/093065 A1 | 5/2020 |

OTHER PUBLICATIONS

Wang et al. "Updated sesame genome assembly and fine mapping of plant height and seed coat color QTLs using a new high-density genetic map" BMC Genomics. 5;17:31, Jan. 2016.

International Search Report for PCT Application No. PCT/IL2018/050520, dated Jul. 22, 2018.

Zhang et al.; Construction of a high-density genetic map for sesame based on large scale marker development by specific length amplified fragment (SLAF) sequencing; BMC Plant Biology, 2013, 13:141.

Office Action dated Apr. 4, 2019 for corresponding U.S. Appl. No. 16/109,346.

Uzin B et al.; Identification of a molecular marker linked to the closed capsule mutant trait in sesame using AFLP; Plant Breeding, Paul Parey Scientific Publ, Berlin, DE, vol. 122, No. 1, Feb. 1, 2003, pp. 95-97.

Dan Mirjafarov; An alternative to GMOs: how to design plants without interfering with the genome; Sep. 14, 2016, retrieved from the Internet: https://agravery.com/uk/posts/show/alternative-gmo-ak-mozna-konstruuvati-roslini-ne-vtrucaucis-v-genom.

Search Report dated Nov. 24, 2020 for corresponding European Application No. EP18802371.7.

Notice of Allowance dated Oct. 17, 2019 for corresponding U.S. Appl. No. 16/109,346, now U.S. Pat. No. 10,577,623, issued Mar. 3, 2020.

European Search Report and Annex dated Mar. 18, 2022 for European Application No. 21204027.3.

Zhou, Rong, et al. "Genome-Wide Association Studies of 39 Seed Yield-Related Traits in Sesame (Sesamum indicum L.)," International Journal of Molecular Sciences 19.9 (Sep. 17, 2018): 2794.

Zhang, Haiyang et al., "TSA: Sesamum indicum Locus_1371_Transcript_1/1_Confidence_1.000_Length_2240 mRNA Sequence", XP055899043, Database accession No. EM_TSA:JP632997 (Jul. 31, 2012).

Wei, Wenliang et al., "TSA: Sesamum indicum Cultivar Zhongzhi 11 Unigene2486mRNA Sequence", XP055899141, Database accession No. EM_TSA:JL323849 (Oct. 2, 2011).

Ashri A., Sesame Breeding. In: Janick J. (ed.). Plant Breeding Reviews vol. 16. John Wiley and Sons, Somerset, NJ, pp. 179-228 (1998).

Wu et al., High-Density Genetic Map Construction and QTLs Analysis of Grain Yield-Related Traits in Sesame (Sesamum indicum L.) Based on RAD-Seq Technology, BMC Riant Biology 14: 274(2014).

Office Action dated Jan. 1, 2021 for U.S. Appl. No. 17/076,027.

Notice of Allowance dated Apr. 7, 2021 tor U.S. Appl. No. 17/076,027.

Wang et al., "Genome sequencing of the high oil crop sesame provides insight into oil biosynthesis" *Genome Biology*, 15:R39, Feb. 27, 2014.

Lander ES and Botstein D., "Mapping mendelian factors underlying quantitative traits using RFLP linkage maps", Genetics. Jan. 1989 ;121(1):pp. 185-199.

Haley CS and Knott SA., "A simple regression method for mapping quantitative trait locl in line crosses using flanking markers" Heredity (Edinb). Oct. 1992;69(4):pp. 315-324.

Jansen, R.C., "Controlling the type I and type II errors in mapping quantitative trait locl" Genetics 138, 1994, pp. 871-881.

Kwoh et al., "Transcription-based amplification system and detection of amplified human immunodeficiency virus type 1 with a bead-based sandwich hybridization format" Proc Natl Acad Sci U S A. Feb. 1989;86(4)pp. 1173-1177.

Guatelli, J.C. et al., "Isothermal, in vitro amplification of nucleic acids by a multienzyme reaction modeled after retroviral replication" Proc Natl Acad Sci U S A, Mar. 1990; 87(5): pp. 1874-1878.

Lomeli H. et al., "Quantitative assays based on the use of replicatable hybridization probes" Clinical Chemistry Sep. 1989, 35 (9) pp. 1826-1831.

Landegren U. et al. "A ligase-mediated gene detection technique" Science. Aug. 26, 1988;241(4869):pp. 1077-1080.

Vos P. et al., "AFLP: a new technique for DNA fingerprinting" Nucleic Acids Res. Nov. 11, 1995;23(21):pp. 4407-4414.

Lincoln, S., Daly, M. & Lander, E.S. , "Mapping genes controlling quantitative traits with MAPMAKER/OTL 1.1." in Whitehead Institute Technical Report vol. 2, Whitehead Institute, Cambridge, Massachusetts, 1994.

Yefim Ronin et al., "Building reliable genetic reaps: different mapping strategies may result in different maps" Natural Science, vol. 2, Issue 6, Jun. 2010, pp. 576-589.

Korol A.B. et al., "Enhanced efficiency of quantitative trait loci mapping analysis based on multivariate complexes of quantitative traits" Genetics. Apr. 2001:157(4): pp. 1789-1803.

Kruglyak, L. and Lander, E S, "A nonparametric approach for mapping quantitative trait loci" Genetics Mar. 1, 1995 vol. 139 No. 3, pp. 1421-1428.

Jansen RC and Stam P., "High resolution of quantitative traits into multiple loci via interval mapping" Genetics. Apr. 1994;136(4):pp. 1447-1455.

Zeng ZB, "Precision mapping of quantitative trait loci" Genetics.:136(4), Apr. 1994; pp. 1457-1468.

Utz and Melchinger, "Biometrics in Plant Breeding", van Oijen, Jansen (eds.) Proceedings of the Ninth Meeting of the Eucarpia Section Biometrics in Plant Breeding, The Netherlands, 1994, pp. 195-204.

Reiter, R.S. et al., "Global and local genome mapping in Arabidopsis thallana by using recombinant inbred lines and random amplified polymorphic DNAs" Proc Natl Acad Sci U S A., Feb. 15, 1992; 89(4): pp. 1477-1481.

Office Action dated Aug. 21, 2019 for U.S. Appl. No. 16/109,346.

International preliminary Report on Patentability dated Nov. 19, 2019 for PCT Application No. PCT/IL2018/050520.

Yol, Engin et al., "A High-Density SNP Genetic Map Construction Using ddRAD-Seq and Mapping of Capsule Shattering Trait in Sesame," Frontiers in Plant Science (2021) 12: 1-13.

Zhang, Haiyang et al., "Development and Validation of Genic-SSR Markers in Sesame by RNA-Seq," Genome Biology (2012) 13: 316.

Zhang, Haiyang et al., "Genetic Analysis and QTL Mapping of Seed Coat Color in Sesame (Sesamum Indicum L.)," PLoS One, May 21, 2013, vol. 8, No. 5, pp. e63898, abstract, p. 2, col. 1, para. 2.

GenBank JP649882 TSA (Sesamum indicum Locus_18970_Transcript_2/2_Confidence_0.8757_Length_628 mRNA sequence) Jul. 30, 2012 (retrieved Mar. 18, 2020). Retrieved from the internet <URL: https://www.ncbi.nim.nih.gov/nuccore/JP649882.1/ > whole doc.

GenBank JL343152 "TSA: Sesamum indicum cultivar Zhongzhi 11 Unigene21112 mRNA sequence") May 31, 2016 (retrieved Mar. 18, 2020). Retrieved from the internet <URL: https://www.ncbi.nim.nih.gov/nuccore/JL343152 > whole doc.

International Search Report and Written Opinion dated Apr. 6, 2020 for International Application No. PCT/US2019/059725.

International Preliminary Report on Patentability dated Apr. 27, 2020 for International Application No. PCT/US2019/059725.

First Action Interview Pilot Program Pre-Interview Communication dated Dec. 21, 2021 for U.S. Appl. No. 17/474,944.

Notice of Allowance dated Feb. 28, 2022 for U.S. Appl. No. 17/474,944.

\* cited by examiner

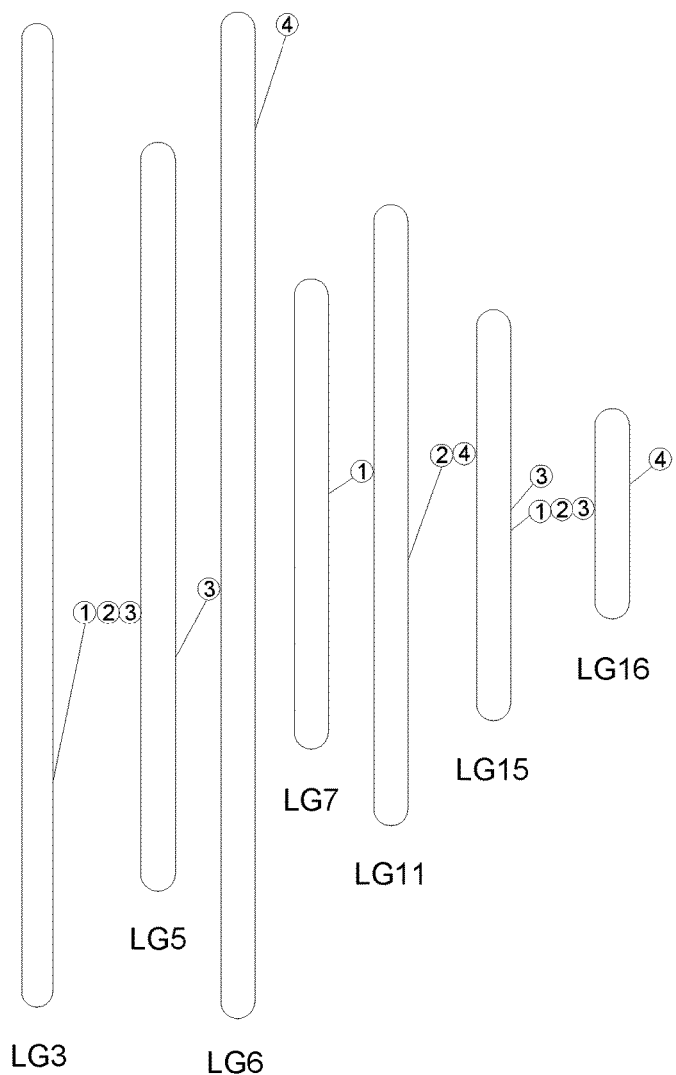

QUANTITATIVE TRAIT LOCI (QTL) ASSOCIATED WITH SHATTER RESISTANT CAPSULES IN SESAME AND USES THEREOF

CROSS REFERENCE TO RELATED APPLICATIONS

This application is a continuation-in-part of U.S. patent application Ser. No. 16/109,346, filed on Aug. 22, 2018, which is a continuation of PCT International Patent Application No. PCT/IL2018/050520, filed on May 14, 2018, which claims the benefit of U.S. Provisional Patent Application No. 62/506,397, filed on May 15, 2017, all of which are incorporated by reference herein in their entirety.

FIELD OF THE INVENTION

The invention is in the field of sesame genetics and breeding. Specifically, the invention relates to genetic improvement for shatter resistant capsules. More specifically, the invention relates to quantitative trait loci (QTL) conferring shatter resistant capsules, and methods thereof, including methods for introgressing the QTL into elite germplasm in a breeding program for shatter resistant capsules.

BACKGROUND OF THE INVENTION

Sesame (*Sesamum indicum*) is an annual plant of the Pedaliaceae family, grown widely in tropical and subtropical areas and have a small (~354 MB) diploid (2n=26) genome. Although sesame is considered to be one of the important and oldest of the oilseed plants, as it has been under cultivation in Asia for over 5000 years, sesame is a crop of developing countries due to its shattering capsules where the crop must harvest manually for preventing losing the seeds, thus requires intensive manual labor. The first and foremost obstacle to complete mechanization is the dehiscence nature of its capsules. Even though some breeding efforts were done during the last seventy years in order to solve it through single gene mutations (ID, GS) and even a combination of few genes (ND and IND varieties), still the majority of the world's sesame (over 99%) is dehiscent (shattering) type.

Accordingly, there exists a need for improved sesame lines and breeding methods for shatter resistant capsules.

SUMMARY OF THE INVENTION

In one aspect, the invention relates to a sesame plant having shatter-resistant capsules or a part thereof, the plant comprising at least one introgressed shatter resistant capsule loci associated with corresponding at least one quantitative trait loci (QTL) having corresponding at least one nucleic acid genetic marker that is associated with shatter resistance of the capsules, wherein the at least one QTL comprises at least one of: QTL 1 with corresponding genetic marker set forth in SEQ ID No. 1 or 9, QTL 2 with corresponding genetic marker set forth in SEQ ID No. 2 or 10, QTL 3 with corresponding genetic marker set forth in SEQ ID No. 3 or 11, QTL 4 with corresponding genetic marker set forth in SEQ ID No. 4 or 12, QTL 5 with corresponding genetic marker set forth in SEQ ID No. 5 or 13, QTL 6 with corresponding genetic markers set forth in SEQ ID No. 6 or 14 and in SEQ ID No. 7 or 15, and QTL 7 with corresponding genetic marker set forth in SEQ ID No. 8 or 16.

In one aspect, the invention relates to a method for identifying a shatter resistant sesame by identifying a plurality of quantitative trait loci ("QTLs") associated with shatter resistant capsules, said method comprising: genotyping a sesame for a plurality of markers associated with said plurality of QTLs, wherein said plurality of QTLs comprises QTLs 1 to 7; and determining whether said sesame comprises an allele of each of said plurality of markers, wherein the presence of said allele indicates the presence of shatter resistant capsule traits in said sesame, thereby identifying said shatter resistant sesame.

In another aspect, the invention relates to a method for producing shatter resistant sesame plants, said method comprising: performing a marker assisted selection to identify a sesame plant comprising an allele of each of a plurality of markers associated with a plurality of quantitative trait loci ("QTLs"), said QTLs associated with shatter resistant capsules, wherein said plurality of QTLs comprises QTLs 1 to 7; and generating sesame plants through a marker assisted breeding, wherein each of said sesame plants comprise said allele of each of said plurality of markers associated with said plurality of QTLs and each of said sesame plants exhibits said shatter resistant capsules.

In yet another aspect, the invention relates to a method of creating a population of sesame plants or seeds for shatter resistant capsules, said method comprising the steps of: genotyping a first population of sesame for a plurality of markers associated with a plurality of quantitative trait loci ("QTLs"), said QTLs associated with said shatter resistant capsules, wherein said plurality of QTLs comprises QTLs 1 to 7; and selecting from said population one or more sesame plants or seeds comprising an allele of each of said plurality of markers; producing from said selected one or more sesame plants or seeds a second population of sesame plants or seeds comprising said plurality of QTLs.

In yet another aspect, the invention relates to a sesame plant or a part thereof comprising: one or more introgressed shatter resistant capsule loci associated with a plurality of quantitative trait loci ("QTLs"), said QTLs associated with shatter resistant capsules, wherein said plurality of QTLs comprises QTLs 1 to 7.

In another embodiment, a sesame plant or a part thereof may comprise one or more introgressed shatter resistant capsule loci associated with a plurality of quantitative trait loci ("QTLs") associated with shatter resistant capsules, wherein said plurality of QTLs comprises QTLs 1 to 7. The shatter resistant capsules may be a full or a partial shatter resistant capsules. The sesame plant or a part thereof may comprise an allele of each of a plurality of markers associated with QTLs 1 to 7.

In another embodiment, the sesame plant part may be a seed, an endosperm, an ovule, pollen, cell, cell culture, tissue culture, plant organ, protoplast, meristem, embryo, or a combination thereof. The sesame plant may be a hybrid.

In another embodiment, a seed of the sesame plant may comprise one or more introgressed shatter resistant capsule loci associated with a plurality of quantitative trait loci ("QTLs") associated with shatter resistant capsules, wherein said plurality of QTLs comprises QTLs 1 to 7.

In an embodiment, a cell of the sesame plant may comprise one or more introgressed shatter resistant capsule loci associated with a plurality of quantitative trait loci ("QTLs") associated with shatter resistant capsules, wherein said plurality of QTLs comprises QTLs 1 to 7. A sesame plant may be grown from the seed comprising one or more introgressed shatter resistant capsule loci associated with a plurality of quantitative trait loci ("QTLs") associated with shatter resistant capsules, wherein said plurality of QTLs comprises QTLs 1 to 7.

In one embodiment, a method for producing a hybrid sesame seed plant may comprise crossing the sesame plant comprising one or more introgressed shatter resistant capsule loci associated with a plurality of quantitative trait loci ("QTLs") associated with shatter resistant capsules, wherein said plurality of QTLs comprises QTLs 1 to 7 with another sesame plant, and obtaining an F1 sesame plant, wherein the F1 sesame plant one or more introgressed shatter resistant capsule loci associated with a plurality of quantitative trait loci ("QTLs") associated with shatter resistant capsules, and wherein said plurality of QTLs comprises QTLs 1 to 7. In other embodiments, sesame plants may be grown from the F1 sesame plant, wherein the F1 sesame plant one or more introgressed shatter resistant capsule loci associated with a plurality of quantitative trait loci ("QTLs") associated with shatter resistant capsules, and wherein said plurality of QTLs comprises QTLs 1 to 7. In another embodiment, a method for producing sesame plants or seeds may comprise growing a sesame plant from the F1 seeds, crossing the F1 sesame plant with a sesame plant, and obtaining F2 seeds from the cross.

In one embodiment, a capsule of a sesame plant comprising one or more introgressed shatter resistant capsule loci associated with a plurality of quantitative trait loci ("QTLs") associated with shatter resistant capsules, wherein said plurality of QTLs comprises QTLs 1 to 7.

In another embodiment, a container may comprise at least one of the capsules of a sesame plant comprising one or more introgressed shatter resistant capsule loci associated with a plurality of quantitative trait loci ("QTLs") associated with shatter resistant capsules, wherein said plurality of QTLs comprises QTLs 1 to 7. The container may comprise a sesame seed comprising one or more introgressed shatter resistant capsule loci associated with a plurality of quantitative trait loci ("QTLs") associated with shatter resistant capsules, wherein said plurality of QTLs comprises QTLs 1 to 7. In other embodiments, the container may be a bag, can, packet, box, or flat.

In a further embodiment, a method of producing sesame seeds may comprise growing a plant comprising one or more introgressed shatter resistant capsule loci associated with a plurality of quantitative trait loci ("QTLs") associated with shatter resistant capsules, wherein said plurality of QTLs comprises QTLs 1 to 7 and harvesting the sesame seeds or capsules. In an embodiment, the harvesting may be done by machine. In an embodiment, a field may comprise a sesame plant comprising one or more introgressed shatter resistant capsule loci associated with a plurality of quantitative trait loci ("QTLs") associated with shatter resistant capsules, wherein said plurality of QTLs comprises QTLs 1 to 7.

BRIEF DESCRIPTION OF THE DRAWINGS

FIG. 1 shows QTLs and linked markers on *Sesamum indicum* linkage groups. The circles with numbers represent marker combination sets ("cassettes"). Circles with the numbers 1, 2, 3, and 4, represent cassettes 1, 2, 3, and 4, respectively.

DETAILED DESCRIPTION OF THE INVENTION

The present subject matter may be understood more readily by reference to the following detailed description which forms a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As employed above and throughout the disclosure, the following terms and abbreviations, unless otherwise indicated, shall be understood to have the following meanings.

In the present disclosure, the singular forms "a", "an", and "the" include the plural reference, and reference to a particular numerical value includes at least that particular value, unless the context clearly indicates otherwise. The term "plurality", as used herein, means more than one. When a range of values is expressed, another embodiment includes from the one particular and/or to the other particular value. Similarly, when values are expressed as approximations, by use of the antecedent "about," it is understood that the particular value forms another embodiment. All ranges are inclusive and combinable.

The term "quantitative trait locus" or "QTL" refers to a polymorphic genetic locus with at least two alleles that differentially affect the expression of a continuously distributed phenotypic trait.

The term "associated with" or "associated" in the context of this invention refers to, e.g., a nucleic acid and a phenotypic trait, that are in linkage disequilibrium, e.g., the nucleic acid and the trait are found together in progeny plants more often than if the nucleic acid and phenotype segregated separately.

The term "linkage disequilibrium" refers to a non-random segregation of genetic loci. This implies that such loci are in sufficient physical proximity along a length of a chromosome that they tend to segregate together with greater than random frequency.

The term "genetically linked" refers to genetic loci that are in linkage disequilibrium and statistically determined not to assort independently. Genetically linked loci assort dependently from 51% to 99% of the time or any whole number value therebetween, preferably at least 60%, 70%, 80%, 90%, 95% or 99%.

The term "proximal" means genetically linked, typically within about 20 centimorgans (cM).

The term "marker" or "molecular marker" refers to a genetic locus (a "marker locus") used as a point of reference when identifying genetically linked loci such as a QTL. The term also refers to nucleic acid sequences complementary to the genomic sequences, such as nucleic acids used as probes.

The term "interval" refers to a continuous linear span of chromosomal DNA with termini defined by and including molecular markers.

The terms "nucleic acid," "polynucleotide," "polynucleotide sequence" and "nucleic acid sequence" refer to single-stranded or double-stranded deoxyribonucleotide or ribonucleotide polymers, or chimeras thereof. As used herein, the term can additionally or alternatively include analogs of naturally occurring nucleotides having the essential nature of natural nucleotides in that they hybridize to single-stranded nucleic acids in a manner similar to naturally occurring nucleotides (e.g., peptide nucleic acids). Unless otherwise indicated, a particular nucleic acid sequence of this invention optionally encompasses complementary sequences, in addition to the sequence explicitly indicated. The term "gene" is used to refer to, e.g., a cDNA and an mRNA encoded by the genomic sequence, as well as to that genomic sequence.

The term "homologous" refers to nucleic acid sequences that are derived from a common ancestral gene through natural or artificial processes (e.g., are members of the same gene family), and thus, typically, share sequence similarity. Typically, homologous nucleic acids have sufficient sequence identity that one of the sequences or its complement is able to selectively hybridize to the other under selective hybridization conditions. The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences have about at least 80% sequence identity, preferably at least 90% sequence identity, and most preferably 95%, 97%, 99%, or 100% sequence identity with each other. A nucleic acid that exhibits at least some degree of homology to a reference nucleic acid can be unique or identical to the reference nucleic acid or its complementary sequence.

The term "isolated" refers to material, such as a nucleic acid or a protein, which is substantially free from components that normally accompany or interact with it in its naturally occurring environment. The isolated material optionally comprises material not found with the material in its natural environment, e.g., a cell. In addition, if the material is in its natural environment, such as a cell, the material has been placed at a location in the cell (e.g., genome or subcellular organelle) not native to a material found in that environment. For example, a naturally occurring nucleic acid (e.g., a promoter) is considered to be isolated if it is introduced by non-naturally occurring means to a locus of the genome not native to that nucleic acid. Nucleic acids which are "isolated" as defined herein, are also referred to as "heterologous" nucleic acids.

The term "recombinant" indicates that the material (e.g., a nucleic acid or protein) has been synthetically (non-naturally) altered by human intervention. The alteration to yield the synthetic material can be performed on the material within or removed from its natural environment or state. For example, a naturally occurring nucleic acid is considered a recombinant nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., WO 1993/022443.

The term "introduced" when referring to a heterologous or isolated nucleic acid refers to the incorporation of a nucleic acid into a eukaryotic or prokaryotic cell where the nucleic acid can be incorporated into the genome of the cell (e.g., chromosome, plasmid, plastid or mitochondrial DNA), converted into an autonomous replicon, or transiently expressed (e.g., transfected mRNA). The term includes such nucleic acid introduction means as "transfection," "transformation" and "transduction."

The term "host cell" means a cell which contains a heterologous nucleic acid, such as a vector, and supports the replication and/or expression of the nucleic acid. Host cells may be prokaryotic cells such as E. coli, or eukaryotic cells such as yeast, insect, amphibian, or mammalian cells. Preferably, host cells are monocotyledonous or dicotyledonous plant cells. In the context of the invention, one particularly preferred monocotyledonous host cell is a soybean host cell.

The term "transgenic plant" refers to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to refer to any cell, cell line, callus, tissue, plant part or plant, the genotype of which has been altered by the presence of heterologous nucleic acid including those transgenic organisms or cells initially so altered, as well as those created by crosses or asexual propagation from the initial transgenic organism or cell. The term "transgenic" as used herein does not encompass the alteration of the genome (chromosomal or extra-chromosomal) by conventional plant breeding methods (e.g., crosses) or by naturally occurring events such as random cross-fertilization, non-recombinant viral infection, non-recombinant bacterial transformation, non-recombinant transposition, or spontaneous mutation.

The term "dicot" refers to the subclass of angiosperm plants also knows as "Dicotyledoneae" and includes reference to whole plants, plant organs (e.g., leaves, stems, roots, etc.), seeds, plant cells, and progeny of the same. Plant cell, as used herein includes, without limitation, seeds, suspension cultures, embryos, meristematic regions, callus tissue, leaves, roots, shoots, gametophytes, sporophytes, pollen, and micro spores.

The term "crossed" or "cross" in the context of this invention means the fusion of gametes via pollination to produce progeny (e.g., cells, seeds, or plants). The term encompasses both sexual crosses (the pollination of one plant by another) and selfing (self-pollination, e.g., when the pollen and ovule are from the same plant).

"Plant," as used herein, refers broadly to the whole plant or any parts or derivatives thereof, such as plant organs (e.g., harvested or non-harvested storage organs, bulbs, tubers, fruits, leaves), plant cells, plant protoplasts, plant cell tissue cultures from which whole plants can be regenerated, plant calli, plant cell clumps, and plant cells that are intact in plants, or parts of plants, such as embryos, pollen, ovules, fruits (e.g., capsule, harvested tissues or organs), flowers, leaves, seeds, clonally propagated plants, roots, stems, root tips. Also, any developmental stage is included, such as seedlings, immature and mature plant parts.

"Variety," as used herein, refers broadly to a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

"Phenotype," as used herein, refers broadly to the observable external and/or physiological appearance of the plant as a result of the interaction between its genotype and its environment. It includes all observable morphological and physiological characteristics.

"Genotype," as used herein, refers broadly to the total of inheritable genetic information of a plant, partly influenced by the environmental factors, which is expressed in the phenotype.

"Hybrid" or "hybrid plant," as used herein, refers broadly to a plant produced by the inter-crossing (cross-fertilization) of at least two different plants or plants of different parent lines. The seeds of such a cross (hybrid seeds) are encompassed, as well as the hybrid plants grown from those seeds and plant parts derived from those grown plants (e.g., seeds).

"F1, F2, seq al.," as used herein, refers broadly to the consecutive related generations following a cross between two parent plants or parent lines. The plants grown from the seeds produced by crossing two plants or lines is called the F1 generation. Selfing the F1 plants results in the F2 generation.

The term "introgression" refers to the transmission of a desired allele of a genetic locus from one genetic background to another. For example, introgression of a desired allele at a specified locus can be transmitted to at least one progeny plant via a sexual cross between two parent plants, where at least one of the parent plants has the desired allele within its genome. Alternatively, for example, transmission of an allele can occur by recombination between two donor genomes, e.g., in a fused protoplast, where at least one of the donor protoplasts has the desired allele in its genome. The desired allele can be, e.g., a transgene or a selected allele of a marker or QTL.

The QTLs of the invention comprise one or more of QTLs 1 to 7. In one embodiment, the alleles of one or more markers linked to QTLs 1-7 are homozygous. In another embodiment, the alleles of one or more markers linked to QTLs 1-7 are heterozygous.

"QTL 1," as used herein refers to a polymorphic genetic locus linked to genetic marker LG3_19205572 in sesame linkage group 3. In one embodiment, the alleles of LG3_19205572 are homozygous. In another embodiment, the alleles of LG3_19205572 are heterozygous. In one embodiment, a first allele of LG3_19205572 may have the base 'C' at position 19205572, and a second allele may have the base 'T' instead of 'C' at position 19205572. The nucleic acid sequence of the first allele of LG3_19205572 marker is set forth in SEQ ID NO: 1, and the nucleic acid sequence of the second allele of LG3_19205572 marker is set forth in SEQ ID NO: 9. All sequences described herein are from Sesame genome version 1. See Wang et al., Genome Biology, 2014, 15(2): R39.

"QTL 2," as used herein refers to a polymorphic genetic locus linked to genetic marker LG5_12832234 in sesame linkage group 5. In one embodiment, the alleles of LG5_12832234 are homozygous. In another embodiment, the alleles of LG5_12832234 are heterozygous. In one embodiment, a first allele of LG5_12832234 may have the base 'C' at position 12832234, and a second allele may have the base 'T' instead of 'C' at position 12832234. The nucleic acid sequence of the first allele of LG5_12832234 marker is set forth in SEQ ID NO: 2, and the nucleic acid sequence of the second allele of LG5_12832234 marker is set forth in SEQ ID NO: 10.

"QTL 3," as used herein refers to a polymorphic genetic locus linked to genetic marker LG6_2739268 in sesame linkage group 6. In one embodiment, the alleles of LG6_2739268 are homozygous. In another embodiment, the alleles LG6_2739268 are heterozygous. In one embodiment, a first allele of LG6_2739268 may have the base 'T' at position 2739268, and a second allele may have the base 'C' instead of 'T' at position 2739268. The nucleic acid sequence of the first allele of LG6_2739268 marker is set forth in SEQ ID NO: 3, and the nucleic acid sequence of the second allele of LG6_2739268 marker is set forth in SEQ ID NO: 11.

"QTL 4," as used herein refers to a polymorphic genetic locus linked to genetic marker LG7_5141423 in sesame linkage group 7. In one embodiment, the alleles of LG7_5141423 are homozygous. In another embodiment, the alleles LG7_5141423 are heterozygous. In one embodiment, a first allele of LG7_5141423 may have the base 'C' at position 5141423, and a second allele may have the base 'G' instead of 'C' at position 5141423. The nucleic acid sequence of the first allele of LG7_5141423 marker is set forth in SEQ ID NO: 4, and the nucleic acid sequence of the second allele of LG7_5141423 marker is set forth in SEQ ID NO: 12.

"QTL 5," as used herein refers to a polymorphic genetic locus linked to genetic marker LG11_8864255 in sesame linkage group 11. In one embodiment, the alleles of LG11_8864255 are homozygous. In another embodiment, the alleles LG11_8864255 are heterozygous. In one embodiment, a first allele of LG11_8864255 may have the base 'C' at position 8864255, and a second allele may have the base 'G' instead of 'C' at position 8864255. The nucleic acid sequence of the first allele of LG11_8864255 marker is set forth in SEQ ID NO: 5, and the nucleic acid sequence of the second allele of LG11_8864255 marker is set forth in SEQ ID NO: 13.

"QTL 6," as used herein refers to a polymorphic genetic locus linked to genetic markers LG15_4900868 and LG15_5315334 in sesame linkage group 15. In one embodiment, the alleles of LG15_4900868 are homozygous. In another embodiment, the alleles LG15_4900868 are heterozygous. In one embodiment, a first allele of LG15_4900868 may have the base 'G' at position 4900868, and a second allele may have the base 'A' instead of 'G' at position 4900868. In one embodiment, the alleles of LG15_5315334 are homozygous. In another embodiment, the alleles LG15_5315334 are heterozygous. In one embodiment, a first allele of LG15_5315334 may have the base 'T' at position 5315334, and a second allele may have the base 'C' instead of 'T' at position 5315334. The nucleic acid sequence of the first allele of LG15_4900868 marker is set forth in SEQ ID NO: 6, the nucleic acid sequence of the second allele of LG15_4900868 marker is set forth in SEQ ID NO: 14, the nucleic acid sequence of the first allele of LG15_5315334 marker is set forth in SEQ ID NO: 7, and the nucleic acid sequence of the second allele of LG15_5315334 marker is set forth in SEQ ID NO: 15.

"QTL 7," as used herein refers to a polymorphic genetic locus linked to genetic marker LG16_1563304 in sesame linkage group 16. In one embodiment, the alleles of LG11_8864255 are homozygous. In another embodiment, the alleles LG16_1563304 are heterozygous. In one embodiment, a first allele of LG16_1563304 may have the base 'A' at position 1563304, and a second allele may have the base 'G' instead of 'A' at position 1563304. The nucleic acid sequence of the first allele of LG16_1563304 marker is set forth in SEQ ID NO: 8, and the nucleic acid sequence of the second allele of LG16_1563304 marker is set forth in SEQ ID NO: 16.

In one aspect, the invention provides a combination of markers wherein the combination comprises LG3_19205572, LG5_12832234, LG6_2739268, LG7_5141423, LG11_8864255, LG15_4900868, LG15_5315334, and LG16_1563304, and wherein the alleles for LG3_19205572, LG7_5141423, and LG15_5315334 are heterozygous.

In another aspect, the invention provides a combination of markers wherein the combination comprises LG3_19205572, LG5_12832234, LG6_2739268, LG7_5141423, LG11_8864255, LG15_4900868, LG15_5315334, and LG16_1563304, and wherein the alleles for LG3_19205572, LG11_8864255, and LG15_5315334 are heterozygous.

In another aspect, the invention provides a combination of markers wherein the combination comprises LG3_19205572, LG5_12832234, LG6_2739268, LG7_5141423, LG11_8864255, LG15_4900868, LG15_5315334, and LG16_1563304, and wherein the alleles for LG3_19205572, LG5_12832234, LG15_4900868, and LG15_5315334 are heterozygous.

In another aspect, the invention provides a combination of markers wherein the combination comprises LG3_19205572, LG5_12832234, LG6_2739268, LG7_5141423, LG11_8864255, LG15_4900868, LG15_5315334, and LG16_1563304, and wherein the alleles for LG6_2739268, LG11_8864255, and LG16_1563304 are heterozygous.

Suitable markers are genetically linked to the QTLs identified herein as associated with shatter resistant capsules, and are within the scope of the present invention. Markers can be identified by any of a variety of genetic or physical mapping techniques. Methods of determining whether markers are genetically linked to a QTL (or to a specified marker) associated with shatter resistant capsules are known to those of skill in the art and include, for example, but not limited to, interval mapping (Lander and Botstein (1989) Genetics 121:185), regression mapping (Haley and Knott (1992) Heredity 69:315) or MQM mapping (Jansen (1994) Genetics 138:871). In addition, physical mapping techniques such as, for example, chromosome walking, contig mapping and assembly, and the like, can be employed to identify and isolate additional sequences useful as markers in the context of the present invention.

In another embodiment, the markers are homologous markers. Homologous markers can be identified by, for example, selective hybridization to a reference sequence. The reference sequence is typically a unique sequence, such as, for example, unique oligonucleotide primer sequences, ESTs, amplified fragments (e.g., corresponding to AFLP markers) and the like, derived from the marker loci of the invention.

In one example, the homologous markers hybridize with their complementary region. For example, two single-stranded nucleic acids "hybridize" when they form a double-stranded duplex. The double stranded region can include the full-length of one or both of the single-stranded nucleic acids, or all of one single stranded nucleic acid and a subsequence of the other single-stranded nucleic acid, or the double stranded region can include a subsequence of each nucleic acid. Selective hybridization conditions distinguish between nucleic acids that are related, e.g., share significant sequence identity with the reference sequence (or its complement) and those that associate with the reference sequence in a non-specific manner. Generally, selective hybridization conditions are described known in the art.

The methods for detecting genetic markers are described known in the art and fully described, for example, in U.S. Pat. Nos. 8,779,233; 6,670,524; 8,692,064; 9,000,258; 8,987,549; 8,637,729; 6,670,524; 6,455,758; 5,981,832; 5,492,547; 9,167,795; 8,656,692; 8,664,472; 8,993,835; 9,125,372; 9,144,220; 9,462,820; 7,250,552; and 9,485,936; and U.S. Patent Application Publications Nos. 2015/0082476; 2011/0154528; 2014/0215657; 2017/0055481; 2015/0150155; and 2015/0101073. Markers corresponding to genetic polymorphisms between members of a population can be detected by numerous methods, described in the art, for example, but not limited to, restriction fragment length polymorphisms, isozyme markers, allele specific hybridization (ASH), amplified variable sequences of the plant genome, self-sustained sequence replication, simple sequence repeat (SSR), single nucleotide polymorphism (SNP), or amplified fragment length polymorphisms (AFLP).

The majority of genetic markers rely on one or more properties of nucleic acids for their detection. For example, some techniques for detecting genetic markers utilize hybridization of a probe nucleic acid to nucleic acids corresponding to the genetic marker. Hybridization formats include, for example, but not limited to, solution phase, solid phase, mixed phase, or in situ hybridization assays. Markers which are restriction fragment length polymorphisms (RFLP), are detected by hybridizing a probe which is typically a sub-fragment (or a synthetic oligonucleotide corresponding to a sub-fragment) of the nucleic acid to be detected to restriction digested genomic DNA. The restriction enzyme is selected to provide restriction fragments of at least two alternative (or polymorphic) lengths in different individuals, and will often vary from line to line. Determining a (one or more) restriction enzyme that produces informative fragments for each cross is a simple procedure, described in the art. After separation by length in an appropriate matrix (e.g., agarose) and transfer to a membrane (e.g., nitrocellulose, nylon), the labeled probe is hybridized under conditions which result in equilibrium binding of the probe to the target followed by removal of excess probe by washing.

Nucleic acid probes to the marker loci can be cloned and/or synthesized. Detectable labels suitable for use with nucleic acid probes include, for example, but not limited to, any composition detectable by spectroscopic, radio-isotopic, photochemical, biochemical, immunochemical, electrical, optical or chemical means. Useful labels include, for example, biotin for staining with labeled streptavidin conjugate, magnetic beads, fluorescent dyes, radiolabels, enzymes, and colorimetric labels. Other labels include ligands which bind to antibodies labeled with fluorophores, chemiluminescent agents, and enzymes. Labeling markers is readily achieved such as, for example, by the use of labeled PCR primers to marker loci.

The hybridized probe is then detected using any suitable technique known in the art, for example autoradiography or other similar detection technique (e.g., fluorography, liquid scintillation counter). Examples of specific hybridization protocols are described in the art.

Amplified variable sequences may refer to amplified sequences of the plant genome which exhibit high nucleic acid residue variability between members of the same species. Organisms have variable genomic sequences and each organism has a different set of variable sequences. Once identified, the presence of specific variable sequence can be used to predict phenotypic traits. Preferably, DNA from the plant serves as a template for amplification with primers that flank a variable sequence of DNA. The variable sequence is amplified and then sequenced.

In vitro amplification techniques are described in the art. Examples of techniques include, for example, but not limited to, the polymerase chain reaction (PCR), the ligase chain reaction (LCR), QP-replicase amplification and other RNA polymerase mediated techniques (e.g., NASBA), are found in Berger, Sambrook and Ausubel (all supra) as well as Mullis et al. (1987) U.S. Pat. No. 4,683,202; PCR Protocols, A Guide to Methods and Applications (Innis et al., eds.) Academic Press Inc., San Diego Academic Press Inc.

San Diego, Calif. (1990) (Innis); Arnheim & Levinson (Oct. 1, 1990) C&EN 36-47; The Journal Of NIH Research (1991) 3, 81-94; (Kwoh et al. (1989) Proc. Natl. Acad. Sci. USA 86, 1173; Guatelli et al. (1990) Proc. Natl. Acad. Sci. USA 87, 1874; Lomell et al. (1989) J. Clin. Chem. 35, 1826; Landegren et al., (1988) Science 241, 1077-1080; Van Brunt (1990) Biotechnology 8, 291-294; Wu and Wallace, (1989) Gene 4, 560; Barringer et al. (1990) Gene 89, 117, and Sooknanan and Malek (1995) Biotechnology 13: 563-564. Improved methods of cloning in vitro amplified nucleic acids are described in Wallace et al., U.S. Pat. No. 5,426,039. Improved methods of amplifying large nucleic acids by PCR are summarized in Cheng et al. (1994) Nature 369: 684, and the references therein, in which PCR amplicons of up to 40 kb are generated.

Oligonucleotides for use as primers, e.g., in amplification reactions and for use as nucleic acid sequence probes are typically synthesized chemically according to, for example, the solid phase phosphoramidite triester method described by Beaucage and Caruthers (1981) Tetrahedron Lett. 22:1859.

Alternatively, self-sustained sequence replication can be used to identify genetic markers. Self-sustained sequence replication refers to a method of nucleic acid amplification using target nucleic acid sequences which are replicated exponentially in vitro under substantially isothermal conditions by using three enzymatic activities involved in retroviral replication: (1) reverse transcriptase, (2) RNAase H, and (3) a DNA-dependent RNA polymerase (Guatelli et al. (1990) Proc Natl Acad Sci USA 87:1874). By mimicking the retroviral strategy of RNA replication by means of cDNA intermediates, this reaction accumulates cDNA and RNA copies of the original target.

Amplified fragment length polymorphisms (AFLP) can also be used as genetic markers (Vos et al. (1995) Nucl Acids Res 23:4407. The phrase "amplified fragment length polymorphism" refers to selected restriction fragments which are amplified before or after cleavage by a restriction endonuclease. The amplification step allows easier detection of specific restriction fragments. AFLP allows the detection large numbers of polymorphic markers and has been used for genetic mapping of plants (Becker et al. (1995) Mol Gen Genet. 249:65; and Meksem et al. (1995) Mol Gen Genet. 249:74.

Allele-specific hybridization (ASH) can be used to identify the genetic markers of the invention. ASH technology is based on the stable annealing of a short, single-stranded, oligonucleotide probe to a completely complementary single-strand target nucleic acid. Detection is via an isotopic or non-isotopic label attached to the probe.

For each polymorphism, two or more different ASH probes are designed to have identical DNA sequences except at the polymorphic nucleotides. Each probe will have exact homology with one allele sequence so that the range of probes can distinguish all the known alternative allele sequences. Each probe is hybridized to the target DNA. With appropriate probe design and hybridization conditions, a single-base mismatch between the probe and target DNA will prevent hybridization. In this manner, only one of the alternative probes will hybridize to a target sample that is homozygous or homogenous for an allele. Samples that are heterozygous or heterogeneous for two alleles will hybridize to both of two alternative probes.

ASH markers are used as dominant markers where the presence or absence of only one allele is determined from hybridization or lack of hybridization by only one probe. The alternative allele may be inferred from the lack of hybridization. ASH probe and target molecules are optionally RNA or DNA; the target molecules are any length of nucleotides beyond the sequence that is complementary to the probe; the probe is designed to hybridize with either strand of a DNA target; the probe ranges in size to conform to variously stringent hybridization conditions, etc.

PCR allows the target sequence for ASH to be amplified from low concentrations of nucleic acid in relatively small volumes. Otherwise, the target sequence from genomic DNA is digested with a restriction endonuclease and size separated by gel electrophoresis. Hybridizations typically occur with the target sequence bound to the surface of a membrane or, as described, for example, in U.S. Pat. No. 5,468,613, the ASH probe sequence may be bound to a membrane.

In one embodiment, ASH data are obtained by amplifying nucleic acid fragments (amplicons) from genomic DNA using PCR, transferring the amplicon target DNA to a membrane in a dot-blot format, hybridizing a labeled oligonucleotide probe to the amplicon target, and observing the hybridization dots by autoradiography.

Single nucleotide polymorphisms (SNP) are markers that consist of a shared sequence differentiated on the basis of a single nucleotide. Typically, this distinction is detected by differential migration patterns of an amplicon comprising the SNP on e.g., an acrylamide gel. However, alternative modes of detection, such as hybridization, e.g., ASH, or RFLP analysis are not excluded.

In yet another basis for providing a genetic linkage map, Simple sequence repeats (SSR), take advantage of high levels of di-, tri-, or tetra-nucleotide tandem repeats within a genome. Dinucleotide repeats have been reported to occur in the human genome as many as 50,000 times with n varying from 10 to 60 or more (Jacob et al. (1991) Cell 67:213. Dinucleotide repeats have also been found in higher plants (Condit and Hubbell (1991) Genome 34:66).

Briefly, SSR data is generated by hybridizing primers to conserved regions of the plant genome which flank the SSR sequence. PCR is then used to amplify the dinucleotide repeats between the primers. The amplified sequences are then electrophoresed to determine the size and therefore the number of di-, tri-, and tetra-nucleotide repeats.

Alternatively, isozyme markers are employed as genetic markers. Isozymes are multiple forms of enzymes which differ from one another in their amino acid, and therefore their nucleic acid sequences. Some isozymes are multimeric enzymes containing slightly different subunits. Other isozymes are either multimeric or monomeric but have been cleaved from the proenzyme at different sites in the amino acid sequence. Isozymes can be characterized and analyzed at the protein level, or alternatively, isozymes which differ at the nucleic acid level can be determined. In such cases any of the nucleic acid based methods described herein can be used to analyze isozyme markers.

In alternative embodiments, in silico methods can be used to detect the marker loci. For example, the sequence of a nucleic acid comprising the marker can be stored in a computer. The desired marker locus sequence or its homolog can be identified using an appropriate nucleic acid search algorithm as provided by, for example, in programs as BLAST or any suitable sequence alignment tool.

Sesame Plants

The sesame plants described herein are not naturally occurring sesame plants. Breeding efforts during the last seventy years have attempt to breed a mechanical harvestable sesame plant capsule using single gene mutations (ID, GS) and even a combination of few genes (ND and IND varieties). These efforts have failed, with the majority of the world's sesame (over 99%) being dehiscent (shattering) type. One reason is that the breeding varieties were developed using classical breeding methodology. Even with the changes in the sesame plants, there are still many agronomical problems such as low germination, plant lodging and low yield potential.

The present invention also provides a shatter resistant sesame plant selected by screening for shatter resistance capsules plant, the selection comprising interrogating genomic nucleic acids for the presence of a marker molecule that is genetically linked to an allele of a QTL associated with shatter resistance capsules in the sesame plant, where the allele of a QTL is also located on a linkage group associated with shatter resistant sesame. A sesame plant or part thereof may comprise at least one quantitative trait loci ("QTLs") associated with shatter resistant capsules, wherein the QTLs comprises QTLs 1 to 7. The sesame plant or part thereof may comprise at least three quantitative trait loci ("QTLs") associated with shatter resistant capsules, wherein the QTLs comprises QTLs 1 to 7. The sesame plant or part thereof may comprise at least one, two, three, four, five, six, or seven quantitative trait loci ("QTLs") associated with shatter resistant capsules, wherein the QTLs comprises QTLs 1 to 7.

Shatter resistant capsules is measured in fully developed capsules having at most 10% seed moisture, and the shatter-resistant capsules are characterized by at least one of the features: (i) at least 80% seed retention after shaking the plant, (ii) at least 80% seed retention after the capsules are turned upside down, (iii) a ratio of at least 5:1 between a total length of the capsule and a length of a zone in which the capsule tips are open, and/or 20-30% of the capsules retain 90-95% of the seeds in fully developed green capsules before drying.

Plants of the invention can be part of or generated from a breeding program. The choice of breeding method may depend on the mode of plant reproduction, the heritability of the trait(s) being improved, and the type of cultivar used commercially (e.g., F1 hybrid cultivar, pureline cultivar). A cultivar may refer to a race or variety of a plant that has been created or selected, and maintained through cultivation.

A method for producing a sesame plant or seed, or a group of plants or seeds, is provided, whereby the plant, or group of plants, produce(s) a seed may comprise one or more introgressed shatter resistant capsule loci associated with a plurality of quantitative trait loci ("QTLs") associated with shatter resistant capsules, wherein said plurality of QTLs comprises QTLs 1 to 7. The method comprises crossing two parent sesame plants or selfing a sesame plant and harvesting the resulting sesame seeds from the cross or selfing, wherein at least one parent is a sesame plant as described herein, or a derivative thereof. Seeds produced by the method are also provided herein, as are sesame plants produced by growing those seeds and sesame capsules harvested from those grown plants.

The method may further comprise the step of growing an F1 hybrid sesame plant obtained from seed obtained from said cross, crossing the F1 sesame plant to another sesame plant, e.g., to one of the parents used, and selecting progeny sesame plants comprising one or more introgressed shatter resistant capsule loci associated with a plurality of quantitative trait loci ("QTLs") associated with shatter resistant capsules, wherein said plurality of QTLs comprises QTLs 1 to 7.

The method may comprise the steps of:
(a) crossing a sesame plant producing sesame seeds comprising one or more introgressed shatter resistant capsule loci associated with a plurality of quantitative trait loci ("QTLs") associated with shatter resistant capsules, wherein said plurality of QTLs comprises QTLs 1 to 7, b) obtaining the F1 seeds from said cross,
(c) selfing and/or crossing the plants obtained from the F1 seeds one or more times with one another or with other sesame plants, and
(d) identifying and selecting progeny plants which produce seeds comprising one or more introgressed shatter resistant capsule loci associated with a plurality of quantitative trait loci ("QTLs") associated with shatter resistant capsules, wherein said plurality of QTLs comprises QTLs 1 to 7; (e) phenotyping the seeds.

Optionally steps (c) and/or (d) can be repeated several times. Crossing in step (c) may also involve backcrossing. In step (d), plants comprising one or more introgressed shatter resistant capsule loci associated with a plurality of quantitative trait loci ("QTLs") associated with shatter resistant capsules, wherein said plurality of QTLs comprises QTLs 1 to 7 may be selected. Thus, the one or more introgressed shatter resistant capsule loci associated with a plurality of quantitative trait loci ("QTLs") associated with shatter resistant capsules, wherein said plurality of QTLs comprises QTLs 1 to 7 can also be used as selection criteria in addition to or as an alternative of shatter resistant capsule traits. The same applies to the methods described herein below, even if only shatter resistant traits are measured.

Phenotyping may comprise detecting one or more introgressed shatter resistant capsule loci associated with a plurality of quantitative trait loci ("QTLs") associated with shatter resistant capsules, wherein said plurality of QTLs comprises QTLs 1 to 7, in the seeds (e.g., by phenotyping one or more populations of step c) above) and selecting rare recombinants or mutants which comprise one or more introgressed shatter resistant capsule loci associated with a plurality of quantitative trait loci ("QTLs") associated with shatter resistant capsules, wherein said plurality of QTLs comprises QTLs 1 to 7. The plants used under a) may be commercially available sesame plant cultivars or breeding lines. Phenotyping can be carried out on a plurality of single seeds independently, preferably grown under the same conditions next to suitable controls, or on a sample composed of (all or parts of) several seeds. When a single seed is used, preferably the mean value is calculated from a representative number of seeds. Phenotyping can be done one or more times. Phenotyping can be carried out at one or more steps of a breeding scheme.

Phenotyping may also comprise an analysis of the one or more introgressed shatter resistant capsule loci associated with a plurality of quantitative trait loci ("QTLs") associated with shatter resistant capsules, wherein said plurality of QTLs comprises QTLs 1 to 7 in the sesame plants produced.

A method for making sesame plants comprising one or more introgressed shatter resistant capsule loci associated with a plurality of quantitative trait loci ("QTLs") associated with shatter resistant capsules, wherein said plurality of QTLs comprises QTLs 1 to 7 may comprise:
(a) optionally, analyzing sesame seeds and/or capsules for one or more introgressed shatter resistant capsule loci associated with a plurality of quantitative trait loci ("QTLs") associated with shatter resistant capsules, wherein said plurality of QTLs comprises QTLs 1 to 7,
(b) crossing plants producing seeds comprising one or more introgressed shatter resistant capsule loci associated with a plurality of quantitative trait loci ("QTLs") associated with shatter resistant capsules, wherein said plurality of QTLs comprises QTLs 1 to 7 with sesame plants to produce F1 hybrids,
(c) selfing and/or (back)crossing F1 hybrid plants one or more times,
(d) selecting progeny plants comprising one or more introgressed shatter resistant capsule loci associated with a plurality of quantitative trait loci ("QTLs") associated with shatter resistant capsules, wherein said plurality of QTLs comprises QTLs 1 to 7 (at harvest and/or after storage) and preferably also for having shatter resistant capsules and
(e) selecting a sesame plant producing seeds comprising one or more introgressed shatter resistant capsule loci associated with a plurality of quantitative trait loci ("QTLs") associated with shatter resistant capsules, wherein said plurality of QTLs comprises QTLs 1 to 7.

Step d) may involve genetic analysis at harvest and/or after storage. In the initial cross, the sesame parent may be a sesame variety, cultivar or breeding line and the other plant may be a sesame variety, cultivar or breeding line. Preferably steps (c) and (d) are repeated several times, so that several cycles of phenotypic recurrent selection are carried out, leading to sesame plants of step (e).

A method of producing an inbred sesame plant comprising one or more introgressed shatter resistant capsule loci associated with a plurality of quantitative trait loci ("QTLs") associated with shatter resistant capsules, wherein said plurality of QTLs comprises QTLs 1 to 7, the method may comprise:
(a) the creation of variable populations of *Sesamum indicum* comprising the steps of crossing a plant or plants producing seeds comprising one or more introgressed shatter resistant capsule loci associated with a plurality of quantitative trait loci ("QTLs") associated with shatter resistant capsules, wherein said plurality of QTLs comprises QTLs 1 to 7 with a plant of the species *Sesamum indicum*,
(b) harvesting the F1 seed from any of the plants used in the cross of (a) and growing F1 plants from the seed harvested,
(c) selfing the plants grown under b) or crossing these plants amongst one another, or crossing these plants with plants of *Sesamum indicum*,
(d) growing plants from the resulting seed harvested under normal plant growing conditions and,
(e) selecting plants producing seeds comprising one or more introgressed shatter resistant capsule loci associated with a plurality of quantitative trait loci ("QTLs") associated with shatter resistant capsules, wherein said plurality of QTLs comprises QTLs 1 to 7, followed by selfing the selected plants, and optionally
(f) repeating the steps (d) and/or (e) until the inbred lines are obtained which are homozygous and can be used as parents in the production of sesame plant hybrids comprising one or more introgressed shatter resistant capsule loci associated with a plurality of quantitative trait loci ("QTLs") associated with shatter resistant capsules, wherein said plurality of QTLs comprises QTLs 1 to 7.

A method for producing a sesame seeds crop from sesame seeds or plants according to the invention and sesame seeds harvested therefrom is provided.

Containers may comprise a plurality of sesame seeds and/or sesame capsules having the phenotypes described herein, as well as containers comprising a plurality of sesame seeds of the above plants or containers comprising a plurality of sesame plants or seedlings. Containers may be of any type, such as bags, cans, tins, trays, boxes, flats. A container may contain at least about 1 pound, 5 pounds, 10 pounds or more of sesames seeds. The container may be in any location, e.g., a store (a grocery store), warehouse, market place, food processor, distributor.

A sesame plant or a part thereof may comprise at least one introgressed shatter resistant capsule loci associated with a plurality of quantitative trait loci ("QTLs") associated with shatter resistant capsules, wherein said plurality of QTLs comprises QTLs 1 to 7. The sesame plant or part thereof may comprise at least three introgressed shatter resistant capsule loci associated with a plurality of quantitative trait loci ("QTLs") associated with shatter resistant capsules, wherein the QTLs comprise QTLs 1 to 7.

The sesame plant may have shatter resistant capsules which are full or partial shatter resistant capsules.

The sesame plant or a part thereof comprises an allele of each of a plurality of markers associated with said QTLs.

The part may be a seed, an endosperm, an ovule, pollen, cell, cell culture, tissue culture, plant organ, protoplast, meristem, embryo, or a combination thereof.

The sesame plant or part may be a hybrid.

Certain embodiments comprise a seed of the sesame plant comprising: one or more introgressed shatter resistant capsule loci associated with a plurality of quantitative trait loci ("QTLs") associated with shatter resistant capsules, wherein said plurality of QTLs comprises QTLs 1 to 7.

Certain embodiments comprise a cell of the sesame plant comprising: one or more introgressed shatter resistant capsule loci associated with a plurality of quantitative trait loci ("QTLs") associated with shatter resistant capsules, wherein said plurality of QTLs comprises QTLs 1 to 7.

Certain embodiments comprise a sesame plant grown from a seed comprising: one or more introgressed shatter resistant capsule loci associated with a plurality of quantitative trait loci ("QTLs") associated with shatter resistant capsules, wherein said plurality of QTLs comprises QTLs 1 to 7

Certain embodiments comprise a method for producing a hybrid sesame seed plant comprising crossing the sesame plant comprising: one or more introgressed shatter resistant capsule loci associated with a plurality of quantitative trait loci ("QTLs") associated with shatter resistant capsules, wherein said plurality of QTLs comprises QTLs 1 to 7 with another sesame plant, and obtaining an F1 sesame plant, wherein the F1 sesame plant comprises one or more introgressed shatter resistant capsule loci associated with a plurality of quantitative trait loci ("QTLs") associated with shatter resistant capsules, and wherein said plurality of QTLs comprises QTLs 1 to 7.

Certain embodiments comprise sesame plants grown from the F1 sesame plant, wherein the F1 sesame plant comprises one or more introgressed shatter resistant capsule loci associated with a plurality of quantitative trait loci ("QTLs") associated with shatter resistant capsules, and wherein said plurality of QTLs comprises QTLs 1 to 7.

Certain embodiments comprise a method for producing sesame plants or seeds comprising growing a sesame plant from the F1 seeds, crossing the F1 sesame plant with a sesame plant, and obtaining F2 seeds from the cross.

Certain embodiments comprise a capsule of the sesame plant which may comprise one or more introgressed shatter resistant capsule loci associated with a plurality of quantitative trait loci ("QTLs") associated with shatter resistant capsules, wherein said plurality of QTLs comprises QTLs 1 to 7.

Certain embodiments comprise a method of producing sesame seeds may comprise planting seeds for a sesame plant comprising: one or more introgressed shatter resistant capsule loci associated with a plurality of quantitative trait loci ("QTLs") associated with shatter resistant capsules, wherein said plurality of QTLs comprises QTLs 1 to 7, growing, and harvesting the sesame seeds or capsules. The harvesting may be done by machine.

Certain embodiments comprise a field comprising the sesame plant which may comprise one or more introgressed shatter resistant capsule loci associated with a plurality of quantitative trait loci ("QTLs") associated with shatter resistant capsules, wherein said plurality of QTLs comprises QTLs 1 to 7.

Sesame seeds and other plant parts described herein can be further processed by a method known to one of skilled in the art. This method may comprise heat treating, for example roasting, the plant parts, preferably sesame seeds. The method may further comprise comminuting, e.g., grinding, the seeds, including seeds following heat treatment (roasting).

Plant breeding methods are described in the art and fully described, for example, in U.S. Pat. Nos. 8,779,233; 6,670,524; 8,692,064; 9,000,258; 8,987,549; 8,637,729; 6,670,524; 6,455,758; 5,981,832; 5,492,547; 9,167,795; 8,656,692; 8,664,472; 8,993,835; 9,125,372; 9,144,220; 9,462,820; and U.S. Patent Application Publication Nos 2015/0082476; 2011/0154528; 2014/0215657; 2017/0055481; 2015/0150155; and 2015/0101073.

Approaches for breeding the plants are described in the art. Selected, non-limiting approaches for breeding the plants are described below. A breeding program can be enhanced using marker assisted selection (MAS) of the progeny of any cross. It is further understood that any commercial and non-commercial cultivars can be utilized in a breeding program.

For highly inheritable traits, a choice of superior individual plants evaluated at a single location can be effective, whereas for traits with low heritability, selection can be based on mean values obtained from replicated evaluations of families of related plants. Popular selection methods commonly include, for example, but not limited to, pedigree selection, modified pedigree selection, mass selection, and recurrent selection. In a preferred embodiment, a backcross or recurrent breeding methods can be used.

The complexity of inheritance influences choice of the breeding method. Backcross breeding can be used to transfer one or a few favorable genes for a highly heritable trait into a desirable cultivar. This approach has been used extensively in breeding. Various recurrent selection techniques are used to improve quantitatively inherited traits controlled by numerous genes. The use of recurrent selection in self-pollinating crops depends on the ease of pollination, the frequency of successful hybrids from each pollination event, and the number of hybrid offspring from each successful cross.

Breeding lines can be tested and compared to appropriate standards in environments representative of the commercial target area(s) for two or more generations. The best lines are candidates for new commercial cultivars; those still deficient in traits may be used as parents to produce new populations for further selection.

One method of identifying a superior plant is to observe its performance relative to other experimental plants and to a widely grown standard cultivar. If a single observation is inconclusive, replicated observations can provide a better estimate of its genetic worth. A breeder can select and cross two or more parental lines, followed by repeated selfing and selection, producing many new genetic combinations.

The development of new sesame cultivars requires the development and selection of sesame varieties, the crossing of these varieties and selection of superior hybrid crosses. The hybrid seed can be produced by manual crosses between selected male-fertile parents or by using male sterility systems, or by using differences between maternal and parental traits heritability in the seed as described in Israel Patent Application Publication IL239702 Hybrids are selected for certain single gene traits such as, for example, herbicide resistance which indicate that the seed is truly a hybrid. Additional data on parental lines, as well as the phenotype of the hybrid, may influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes. New cultivars can be evaluated to determine which have commercial potential.

Pedigree breeding is used commonly for the improvement of self-pollinating crops. Two parents who possess favorable, complementary traits are crossed to produce an F1. An F2 population is produced by selfing one or several F1's. Selection of the best individuals in the best families is selected. Replicated testing of families can begin in the F4 generation to improve the effectiveness of selection for traits with low heritability. At an advanced stage of inbreeding (e.g., F6 and F7), the best lines or mixtures of phenotypically similar lines are tested for potential release as new cultivars.

Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting parent is expected to have the attributes of the recurrent parent (e.g., cultivar) and the desirable trait transferred from the donor parent.

Other suitable methods such as, for example, single-seed descent procedure and a multiple-seed procedure can also be used.

The single-seed descent procedure in the strict sense refers to planting a segregating population, harvesting a sample of one seed per plant, and using the one-seed sample to plant the next generation. When the population has been advanced from the F2 to the desired level of inbreeding, the plants from which lines are derived will each trace to different F2 individuals. The number of plants in a population declines each generation due to failure of some seeds to germinate or some plants to produce at least one seed. As a result, not all of the F2 plants originally sampled in the population will be represented by a progeny when generation advance is completed.

In a multiple-seed procedure, breeders commonly harvest one or more capsules from each plant in a population and thresh them together to form a bulk. Part of the bulk is used to plant the next generation and part is put in reserve.

Other breeding methods are described in the art, for example, in Fehr, Principles of Cultivar Development Vol. 1, (1987).

The present invention also provides for parts of the plants of the present invention. Plant parts, without limitation, include seed, endosperm, ovule and pollen. In a particularly preferred embodiment of the present invention, the plant part is a seed.

On Oct. 29, 2021, a deposit seeds of EQUI-NOM LTD. sesame line 20-95289 was made by EQUI-NOM LTD. under the provisions of the Budapest Treaty with International Patent Organism Depositary (IPOD), Biological Resource Center, National Institute of Technology and Evaluation, 2-5-8 Kazusakamatari, Kisarazu, Chiba 292-0818, Japan, and the deposit, which was received on Jan. 11, 2022, was given IPOD Receipt Number FERM ABP-22438. This deposit will be maintained in the IPOD depository for a period of 30 years after the deposition. Should the seeds from the EQUI-NOM LTD. sesame line 20-95289 deposited with the IPOD become unviable, the deposit will be replaced by EQUI-NOM LTD. upon request.

Sesame plant and or part thereof EQUI-NOM LTD. sesame line 20-95289 is an exemplary variety, which exhibits improved shatter-resistant capsule characteristics and desirable characteristics which make it a commercially suitable sesame line.

EQUI-NOM LTD. sesame line 20-95289 comprises shatter resistant capsule loci associated with QTL 1 to QTL 7, wherein each of QTLs 1-7 is linked to at least one nucleic acid genetic marker that is associated with shatter resistance of the capsules, wherein the genetic markers are arranged in four marker cassettes: cassette 1 comprising LG3_19205572, LG7_5141423, LG15_5315334, or a combination thereof, wherein the alleles for said LG3_19205572, LG7_5141423, and LG15_5315334 are homozygous, marker cassette 2 comprising LG3_19205572, LG11_8864255, LG15_5315334, or a combination thereof, wherein the alleles for said LG3_19205572, LG11_8864255, and LG15_5315334 are homozygous, marker cassette 3 comprising LG3_19205572, LG5_12832234, LG15_4900868, LG15_5315334, or a combination thereof, wherein the alleles for said LG3_19205572, LG5_12832234, LG15_4900868, and LG15_5315334 are homozygous, and marker cassette 4 comprising LG6_2739268, LG11_8864255, LG16_1563304, or combination thereof, wherein the alleles for said LG6_2739268, LG11_8864255, and LG16_1563304 are homozygous.

Plants or parts thereof of the present invention may be grown in culture and regenerated. Methods for the regeneration of sesame plants from various tissue types and methods for the tissue culture of sesame are known in the art (See, for example, George et al., 1987, Ann Bot., vol. 60 (1), pages 17-21; Were et al., 2006, Plant Cell Tiss Organ Cult, vol. 85, page 235). The present invention also provides a shatter resistant sesame plant selected for by screening for shatter resistant capsules plant, the selection comprising interrogating genomic nucleic acids for the presence of a marker molecule that is genetically linked to an allele of a QTL associated with shatter resistant capsules in the sesame plant, where the allele of a QTL is also located on a linkage group associated with shatter resistant sesame.

The genetic linkage of additional marker molecules can be established by a gene mapping model such as, for example, without limitation, the flanking marker model reported by Lander and Botstein, Genetics, 121:185-199 (1989), and the interval mapping, based on maximum likelihood methods described by Lander and Botstein, Genetics, 121:185-199 (1989), and implemented in the software package MAPMAKER/QTL (Lincoln and Lander), Mapping Genes Controlling Quantitative Traits Using MAPMAKER/QTL, Whitehead Institute for Biomedical Research, Massachusetts, (1990). Additional software includes Qgene, Version 2.23 (1996), Department of Plant Breeding and Biometry, 266 Emerson Hall, Cornell University, Ithaca, N.Y., the manual of which is herein incorporated by reference in its entirety). Additional software includes MultiPoint program (Yefim Ronin, Natural Science, Vol. 2, No. 6, 576-589 (2010)), which is based on the Traveling Salesperson Problem (TSP). The mapping is done by employing a series of increasing recombination thresholds in order to minimalize the chance of mixing markers from different chromosome. By each step of increasing the recombination thresholds the shorter linkage groups have the potential to merge into a longer of the linkage groups.

A maximum likelihood estimate (MLE) for the presence of a marker is calculated, together with an MLE assuming no QTL effect, to avoid false positives. A login of an odds ratio (LOD) is then calculated as: LOD=$\log_{10}$ (MLE for the presence of a QTL/MLE given no linked QTL). The LOD score essentially indicates how much more likely the data are to have arisen assuming the presence of a QTL versus in its absence. The LOD threshold value for avoiding a false positive with a given confidence, say 95%, depends on the number of markers and the length of the genome. Graphs indicating LOD thresholds are set forth in Lander and Botstein, Genetics, 121:185-199 (1989), and further described by Ares and Moreno-Gonzalez, Plant Breeding, Hayward, Bosemark, Romagosa (eds.) Chapman & Hall, London, pp. 314-331 (1993). QTL prediction was done using MultiQTL program based on the linkage maps that were merged by Multipoint and the F2 population phenotype data. MultiQTL use multiple interval mapping (MIM). MultiQTL significance is computed with permutation, bootstrap tools and FDR for total analysis. (Korol et al. Enhanced Efficiency of Quantitative Trait Loci Mapping Analysis Based on Multivariate Complexes of Quantitative Traits, Genetics. 2001 April; 157(4): 1789-1803.

Additional models can be used. Many modifications and alternative approaches to interval mapping have been reported, including the use of non-parametric methods (Kruglyak and Lander, Genetics, 139:1421-1428 (1995), the entirety of which is herein incorporated by reference). Multiple regression methods or models can be also be used, in which the trait is regressed on a large number of markers (Jansen, Biometrics in Plant Breed, van Oijen, Jansen (eds.) Proceedings of the Ninth Meeting of the Eucarpia Section Biometrics in Plant Breeding, The Netherlands, pp. 116-124 (1994); Weber and Wricke, Advances in Plant Breeding, Blackwell, Berlin, 16 (1994)). Procedures combining interval mapping with regression analysis, whereby the phenotype is regressed onto a single putative QTL at a given marker interval, and at the same time onto a number of markers that serve as 'cofactors,' have been reported by Jansen and Stam, Genetics, 136:1447-1455 (1994) and Zeng, Genetics, 136:1457-1468 (1994). Generally, the use of cofactors reduces the bias and sampling error of the estimated QTL positions (Utz and Melchinger, Biometrics in Plant Breeding, van Oijen, Jansen (eds.) Proceedings of the Ninth Meeting of the Eucarpia Section Biometrics in Plant Breeding, The Netherlands, pp. 195-204 (1994), thereby improving the precision and efficiency of QTL mapping (Zeng, Genetics, 136:1457-1468 (1994)). These models can be extended to multi-environment experiments to analyze genotype-environment interactions (Jansen et al., Theo. Appl. Genet. 91:33-37 (1995).

Selection of appropriate mapping populations is important to map construction. The choice of an appropriate mapping population depends on the type of marker systems employed (Tanksley et al., Molecular mapping of plant chromosomes. chromosome structure and function: Impact of new concepts J. P. Gustafson and R. Appels (eds.). Plenum Press, New York, pp. 157-173 (1988), the entirety of which is herein incorporated by reference). Consideration must be given to the source of parents (adapted vs. exotic) used in the mapping population. Chromosome pairing and recombination rates can be severely disturbed (suppressed) in wide crosses and generally yield greatly reduced linkage distances. Wide crosses will usually provide segregating populations with a relatively large array of polymorphisms when compared to progeny in a narrow cross.

An F2 population is the first generation of selfing after the hybrid seed is produced. In one example, a single F1 plant can be selfed to generate a population segregating for all the genes in Mendelian (1:2:1) fashion. Maximum genetic information is obtained from a completely classified F2 population using a codominant marker system (Mather, Measurement of Linkage in Heredity: Methuen and Co., (1938), the entirety of which is herein incorporated by reference). In the case of dominant markers, progeny tests (e.g., F3, BCF2) are required to identify the heterozygotes, thus making it equivalent to a completely classified F2 population. However, this procedure is often prohibitive because of the cost and time involved in progeny testing. Progeny testing of F2 individuals is often used in map construction where phenotypes do not consistently reflect genotype (e.g., disease resistance) or where trait expression is controlled by a QTL. Segregation data from progeny test populations (e.g., F3 or BCF2) can be used in map construction. Marker-assisted selection can then be applied to cross progeny based on marker-trait map associations (F2, F3), where linkage groups have not been completely disassociated by recombination events (e.g., maximum disequilibrium).

Recombinant inbred lines (RIL) (genetically related lines; usually >F5, developed from continuously selfing F2 lines towards homozygosity) can be used as a mapping population. Information obtained from dominant markers can be maximized by using RIL because all loci are homozygous or nearly so. Under conditions of tight linkage (e.g., about <10% recombination), dominant and co-dominant markers evaluated in RIL populations provide more information per individual than either marker type in backcross populations (Reiter et al., Proc. Natl. Acad. Sci. (U.S.A.) 89:1477-1481 (1992)). However, as the distance between markers becomes larger (e.g., loci become more independent), the information in RIL populations decreases dramatically when compared to codominant markers.

Backcross populations (e.g., generated from a cross between a successful variety (recurrent parent) and another variety (donor parent) carrying a trait not present in the former) can be utilized as a mapping population. A series of backcrosses to the recurrent parent can be made to recover most of its desirable traits. Thus, a population is created consisting of individuals nearly like the recurrent parent but each individual carries varying amounts or mosaic of genomic regions from the donor parent. Backcross populations can be useful for mapping dominant markers if all loci in the recurrent parent are homozygous and the donor and recurrent parent have contrasting polymorphic marker alleles (Reiter et al., Proc. Natl. Acad. Sci. (U.S.A.) 89:1477-1481 (1992)). Information obtained from backcross populations using either codominant or dominant markers is less than that obtained from F2 populations because one, rather than two, recombinant gametes are sampled per plant. Backcross populations, however, are more informative (at low marker saturation) when compared to RILs as the distance between linked loci increases in RIL populations (e.g., about 0.15% recombination). Increased recombination can be beneficial for resolution of tight linkages, but may be undesirable in the construction of maps with low marker saturation.

Near-isogenic lines (NIL) created by many backcrosses to produce an array of individuals that are nearly identical in genetic composition except for the trait or genomic region under interrogation can be used as a mapping population. In mapping with NILs, only a portion of the polymorphic loci are expected to map to a selected region.

Bulk segregant analysis (BSA) is a method developed for the rapid identification of linkage between markers and traits of interest (Michelmore, et al., Proc. Natl. Acad. Sci. (U.S.A.) 88:9828-9832 (1991)). In BSA, two bulked DNA samples are drawn from a segregating population originating from a single cross. These bulks contain individuals that are identical for a particular trait (resistant or susceptible to particular disease) or genomic region but arbitrary at unlinked regions (e.g., heterozygous). Regions unlinked to the target region will not differ between the bulked samples of many individuals in BSA.

An alternative to traditional QTL mapping involves achieving higher resolution by mapping haplotypes, versus individual markers (Fan et al. 2006 Genetics). This approach tracks blocks of DNA known as haplotypes, as defined by polymorphic markers, which are assumed to be identical by descent in the mapping population. This assumption results in a larger effective sample size, offering greater resolution of QTL. Methods for determining the statistical significance of a correlation between a phenotype and a genotype, in this case a haplotype, may be determined by any statistical test known in the art and with any accepted threshold of statistical significance being required. The application of particular methods and thresholds of significance are described in the art.

In another aspect, overlapping sets of clones can be derived by using the available markers of the present invention to screen, for example, BAC, PAC, bacteriophage P1, or cosmid libraries. In addition, hybridization approaches can be used to convert the YAC maps into BAC, PAC, bacteriophage P1, or cosmid contig maps. Entire YACs and products of inter-Alu-PCR as well as primer sequences from appropriate STSs can be used to screen BAC, PAC, bacteriophage P1, or cosmid libraries. The clones isolated for any region can be assembled into contigs using STS content information and fingerprinting approaches (Sulston et al., Comput. Appl. Biosci. 4:125-132 (1988)).

According to another embodiment, the degeneracy of the genetic code, which allows different nucleic acid sequences to code for the same protein or peptide, is known in the literature. As used herein a nucleic acid molecule is degenerate of another nucleic acid molecule when the nucleic acid molecules encode for the same amino acid sequences but comprise different nucleotide sequences. An aspect of the present invention is that the nucleic acid molecules of the present invention include nucleic acid molecules that are degenerate of the nucleic acid molecule that encodes the protein(s) of the quantitative trait alleles.

Another aspect of the present invention is that the nucleic acid molecules of the present invention include nucleic acid molecules that are homologues of the nucleic acid molecule that encodes the one or more of the proteins associated with the QTL.

Exogenous genetic material may be transferred into a plant by the use of a DNA plant transformation vector or construct designed for such a purpose. A particularly preferred subgroup of exogenous material comprises a nucleic acid molecule of the present invention (See, Plant Molecular Biology: A Laboratory Manual, eds. Clark, Springer, New York (1997)).

In another aspect, a construct or vector may include the endogenous promoter of the scatter resistance QTL of the present invention. The characteristic of scatter resistance might best be achieved by expressing the identified QTL protein with the endogenous promoter. Alternatively, a heterologous promoter may be selected to express the protein or protein fragment of choice. These promoters may be operably linked to a polynucleotide sequence encoding the protein corresponding to the scatter resistance QTL. The heterologous promoter may be one that is selected based upon maturation or flowering time, in that timing of expression of the desired protein may be critical to the parameters affecting the scatter disease resistance trait. Effective expression of the scatter disease resistance QTL may require promoters that express in specific tissue types.

All patents and literature references cited in the present specification are hereby incorporated by reference in their entirety.

The following examples are provided to supplement the prior disclosure and to provide a better understanding of the subject matter described herein. These examples should not be considered to limit the described subject matter. It is understood that the examples and embodiments described herein are for illustrative purposes only and that various modifications or changes in light thereof will be apparent to persons skilled in the art and are to be included within, and can be made without departing from, the true scope of the invention.

EXAMPLES

Example 1

QTL for Shatter Resistant Sesame

This innovation presents a methodology of breeding sesame lines bearing shatter resistant capsules. 99% of the sesame plants grown worldwide are harvested manually. The first and foremost obstacle to complete mechanization for this important crop is the dehiscence nature of its capsules. This innovative method includes the collection of worldwide sesame lines, the creation of F2 linkage populations, massive phenotyping and genotyping of thousands of sesame lines, prediction of QTL's affecting the shattering resistance trait, and the establishing of unique marker combinations (a "marker cassette") for shattering resistant sesame lines never found before in commercial or natural lines.

Disclosed breeding methodology is based on the discovery of the Target Product Genomic Code (TPGC). The Target Product (TP) is define in advance based on market requirements. It includes a set of desired attributes (traits) that are available in natural genetic variations and the Genomic Code (GC), which is a set of genomic regions that affect the Target Products' traits. Algorithms take the GC, which is composed of a quantitative trait locus (QTL) database linked to the TP, and define the Target Product Genomic Code (TPGC). The algorithms calculate multiple genomic interactions, including effects of heterosis and epistasis, and maximize the genomic potential of specific plants for the development of new varieties. The breeding program discovers the TPGC, then by crossing and selfing we progress until we achieve a product which contains the specific GC we discovered. A typical breeding project includes the following breeding and technical cycles:

Trait Discovery—where a broad spectrum of varieties from different geographies and worldwide sources are grown and phenotyped in order to discover new traits that can potentially be combined to create the new product.

Trait Blend—a crossing cycle based on phenotypic assumption, where we mix and combine the different traits. The initial trait cycle is followed by an additional cycle to create an F2 population, which will provide the basis for algorithmic analysis that will lead to the TPGC construction.

TPGC Discovery—the most important phase where every single plant is phenotyped and genotyped to produce a linkage map, discover the QTLs and discover the TPGC using our proprietary technology.

Line Validation 1.1—the first year of validating line version 1. These lines are based on millions of in silico selections and are defined as the project's pioneer varieties.

Line Validation 1.2—the second year of validating line version 1.

Pre-commercial 1.3—the third year and final validation of line version 1.

Trait TPGC Blend—in this the phase we perform accurate crossing based on our proprietary algorithm, calculating the most efficient way to reach the best TPGC. The crossing is performed after in silico selection of millions of combinations. The trait TPGC blend phase is followed by an additional cycle to produce an F2 population for a second GC discovery. It is important to note that this phase is based on our algorithm, unlike the Trait Blend phase that is based on phenotype assumptions. Defining the TP for sesame includes identifying the shatter resistant trait to enable harvesting mechanically. To identify the shatter resistant capsules traits, a set of phenotype traits where developed to correlate with measured seed retention and capsule structure. The unique combination between the capsule structure and seed retention enable it to be harvested mechanically but still enabling the seed to release easily by the thresher in the combine. For the unique combination, identifying a plurality of quantitative trait loci ("QTLs") associated with it (GC) completes the TPGC for breeding sesame for mechanical harvesting.

The trait discovery is based on germplasm included five hundreds different sesame lines that were obtained from the U.S. National Plant Germplasm System (NPGC) and courtesy of Prof. Amram Ashri's sesame germplasm collection (Ashri, 1998). Screening for trait discovery was based on allocating traits related to capsule structure and capsule retention of the seeds.

150 different lines were produced for trait blend—crosses, executed based on the potential for enrichment of genomic diversity as creating a new complex of traits for the shatter resistant capsules as the initial step for a TP directed breeding program for shattering resistant sesame lines. The resulted F1 hybrids were later self-crossed to create F2 linkage populations that showed phenotypic segregation.

The F2 population then planted in 6 different environments for discovering the TPGC, including shattering resistant capsules traits. After screening 15000 individuals, a set of ~3000 representative was selected. The selected individuals F2 were massively phenotyped for three shatter resistant capsule (SRC) components:

SRC1: Evaluating the rate of the seed retention by shaking the plant and counting the amount seeds that are falling down to the ground.

SRC2: Evaluating the rate of the seed retention after the capsules are turned upside down, by counting the amount of the seeds that remain inside the capsules.

SRC3: Measuring the ratio between the total length of the capsule and the length of the zone in which the capsule tips are open, by measuring each of the lengths using a ruler.

All the shatter resistant capsule trait's components were summarized into one representative trait which was named the shatter resistant capsule trait. The selected ~3000 individuals were genotyped under examination of a panel with 400 markers, based on single nucleotide polymorphism (SNP). These 400 markers' panel is directly designed based on parental lines RNA-sequences of each linkage F2 population. The panel was designed to maximize the chance to have the largest number of common segregate SNP's in order to create highly similar linkage maps for all observed populations.

Mapping Population

The computation of linkage maps is executed on each linkage F2 population based on genotyping results. Linkage maps were computed with MultiPoint, an interactive package for ordering multi-locus genetic maps, and verification of maps based on resampling techniques.

QTL Discovery

QTL discovery related to shattering resistance was executed with MultiQTL package. The program produced linkage maps that were merged by Multipoint and the F2 population phenotype data. MultiQTL use multiple interval mapping (MIM). MultiQTL significance is computed with permutation, bootstrap tools and FDR for total analysis. The inventors have analyzed the linkage maps of all eight F2 populations and the information relating to the three shatter resistant capsule traits over all genotyped plants that belong to the F2 populations. The prediction of QTL was in a "one trait to-one marker" model, meaning that for all markers that constructed the linkage maps, each trait was tested independently against each one of the markers. The results point to 8 markers from 7 different linkage groups that are representing QTL's related to shattering resistance as described in table I. Each population presented a different marker—cassettes related to shattering resistance but still some populations shared a subset of common markers with other populations. The verities of marker-cassettes were summarize as described in FIG. 1.

Significance and Co-Occurrences of Shattering Resistant Capsules Markers

The QTL analysis provided the set of markers that represent QTL related to shattering resistant capsules in sesame for each linkage F2 population separately. In order to strengthen the significance of each marker, an in-house algorithm was developed to observe genotype-phase of each marker related to QTL/trait in all linkage F2 populations in different environments. The occurrence of shattering resistance capsules marker in two or more linkage F2 population (repetitive markers) strengthen its significance as representative for shattering resistant capsules QTL. In addition, the co-occurrence of non-repetitive and repetitive markers related to shattering resistance capsules in a given population was observed for the design of "marker-cassettes" that provides the genetic signature for shattering resistant capsules in sesame lines.

In-Silico Self- and Cross-Self Based Breeding Program

Based on the QTL prediction, which provide the effect of each phase of a given marker for each of the three shatter resistant capsule traits, three different algorithms for the simulation and prediction of the genotypic state of self, cross-self and hybrid plant was in-house developed for processing the TPGC blend. The TPGC blend combines QTL's from different populations together into a single plant to increase similarity of the discovered TPGC to an exciting product, which contains a unique cassette of QTL's for shatter resistant capsule which never exist before. The algorithms design in silico millions of selfing combination from F2 to F8, millions of new combination of F1 and then selfing to F8 and millions of F1 hybrids to create hybrid variety. This, in order to measure the potential for each of the 3000 plants to acquire the shatter resistant capsules in the right combination at the right phase. After running the analysis among ~3000 plants, 200 higher score plants were chosen for the selfing, cross selfing and hybrid programs.

Validation of Shatter Resistant Capsules Lines

After the determination of which plants have the highest potential to acquire shattering resistant capsules based on genetic code, it is important to preserve this potential in next generations. In order to follow the genetic code of the shattering resistant capsules "marker cassettes", the offspring of each chosen lines (the next generation) were genotyped based on the shattering resistant capsules "marker cassettes". Only offspring's that present the previous generation "marker cassette" for shattering resistant capsules were selected and forwarded to the next generation. This procedure ensures the maintenance of the shattering resistant capsules trait and "marker-cassette" for each shattering resistant line. This invention presents a methodology for the design of 4 marker—cassettes that point, with one marker cassette or more, on shattering resistant capsules sesame lines.

In one embodiment, marker cassette 1 comprises the genetic markers LG3_19205572, LG7_5141423, LG15_5315334, or a combination thereof. In some embodiments the alleles for said LG3_19205572, LG7_5141423, and LG15_5315334 are homozygous or heterozygous.

In one embodiment, marker cassette 2 comprises LG3_19205572, LG11_8864255, LG15_5315334, or a combination thereof. In some embodiments the alleles for said LG3_19205572, LG11_8864255, and LG15_5315334 are homozygous or heterozygous.

In one embodiment, marker cassette 3 comprises LG3_19205572, LG5_12832234, LG15_4900868, LG15_5315334, or a combination thereof. In some embodiments the alleles for said LG3_19205572, LG5_12832234, LG15_4900868, and LG15_5315334 are homozygous or heterozygous.

In one embodiment, marker cassette 4 comprises LG6_2739268, LG11_8864255, LG16_1563304, or combination thereof. In some embodiments the alleles for said LG6_2739268, LG11_8864255, and LG16_1563304 are homozygous or heterozygous.

TABLE 1

Marker cassettes and QTL

| Marker name | LG | Position | QTL | SRC (2) | Ref. (1) allele | alternative allele | cassette 1 | cassette 2 | cassette 3 | cassette 4 | P-value (3) |
|---|---|---|---|---|---|---|---|---|---|---|---|
| LG3_19205572 | 3 | 19205572 | 1 | SRC3 | C | T | CC/CT | CC/CT | CC/CT | . | 0.05 |
| LG5_12832234 | 5 | 12832234 | 2 | SRC3 | C | T | . | . | CC/CT | . | 0.025 |
| LG6_2739268 | 6 | 2739268 | 3 | SRC3 | T | C | . | . | . | CC/CT | 0.045 |
| LG7_5141423 | 7 | 5141423 | 4 | SRC1, SRC3 | C | G | CC/CG | . | . | . | 0.0075 |
| LG11_8864255 | 11 | 8864255 | 5 | SRC3 | C | G | . | CC/CG | . | CC/CG | 0.003 |
| LG15_4900868 | 15 | 4900868 | 6 | SRC1, SRC2, SRC3 | G | A | . | . | AA/AG | . | 0.0005 |
| LG15_5315334 | 15 | 5315334 | 6 | SRC1, SRC2, SRC3 | T | C | CC/CT | CC/CT | CC/CT | . | 0.0005 |
| LG16_1563304 | 16 | 1563304 | 7 | SRC3 | A | G | . | . | . | GG/AG | 0.038 |

(1) Reference allele based on Sesamum indicum reference Genome V1.0 (Wang L, Yu S, Tong C, et al. Genome sequencing of the high oil crop sesame provides insight into oil biosynthesis. Genome biology, 2014, 15(2): R39).
(2) The SRC trait that is affected by a given marker.
(3) The p-value is the significance level of single- QTL analysis commuted by MultiQTL program.

TABLE 2

Heterozygous Allele Effect

| Marker name | QTL | Reference Allele Effect | | Alternative Allele Effect | | Heterozygous Allele Effect | | p-value |
|---|---|---|---|---|---|---|---|---|
| | | Effect | STD | Effect | STD | Effect | STD | |
| LG3_19205572 | 1 | 141 | 25 | 94 | 27 | 132 | 24 | 0.05 |
| LG5_12832234 | 2 | 18.4 | 1.4 | 12.5 | 1.25 | 14.2 | 1.8 | 0.025 |
| LG6_2739268 | 3 | 13.8 | 1.2 | 17.6 | 1.8 | 13.3 | 2.45 | 0.045 |
| LG7_5141423 | 4 | 17.4 | 1.1 | 14.2 | 1 | 12.2 | 1.5 | 0.0075 |
| LG11_8864255 | 5 | 25.8 | 1.6 | 21.4 | 0.8 | 22.8 | 0.9 | 0.003 |
| LG15_4900868 | 6 | 14.5 | 0.6 | 28 | 0.6 | 24.7 | 0.8 | 0.0005 |
| LG15_5315334 | 6 | 13.6 | 0.4 | 22.1 | 0.55 | 20.5 | 0.65 | 0.0005 |
| LG16_1563304 | 7 | 23.4 | 2 | 32 | 2.3 | 23.1 | 2.9 | 0.038 |

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

SEQUENCE LISTING

<160> NUMBER OF SEQ ID NOS: 16

<210> SEQ ID NO 1
<211> LENGTH: 301
<212> TYPE: DNA
<213> ORGANISM: Sesamum indicum

<400> SEQUENCE: 1
cctttagcag ggcatcactc tcttcaacat cgtactgcac cgagaggaat ttcgaagtga        60
gaaaaacttg gggctccgac acttccccttt tgctgtcgtt ttgaaaagtg agcttcaatt       120
tcgccaaatt atccaacaat ttgcacgaga ctttattaaa gaacacggag ctctcgctgt       180

```
cgaactccga cgtaactcgc agcttcggcc gacccatttg gaagagcccc agaaaaccgc    240
cgcctttcga accgccgtcg tccacggcgg gggatggtgg tggagacaga aatagggtt     300 g                                                                   301
```

<210> SEQ ID NO 2
<211> LENGTH: 301
<212> TYPE: DNA
<213> ORGANISM: Sesamum indicum

<400> SEQUENCE: 2

```
ccgggccaca actgatgctt attgtgttgc caaatatggt cagaagtggg tcaggacaag    60
gacaatcatc gacagttttg ctcctaaatg gaatgagcag tatacttggg aagttttga    120 tccttgcact gttgtcacca ttggtgtatt cgataattgt catctgcaag gtggagataa    180
agctggaagg gattcaagaa tgggaaggt aagaattcgc ctttcaactc tggaaacaga    240
ccgtgtgtac actcattctt atcctcttct agttttgcat ccttccgggg taaaaaagat    300
g                                                                   301
```

<210> SEQ ID NO 3
<211> LENGTH: 301
<212> TYPE: DNA
<213> ORGANISM: Sesamum indicum

<400> SEQUENCE: 3

```
ttagggcgtc gaattacttg gacgcgccga gcaagctagc ctgctgcaac tcaagctcgt    60
tgagctgctg ctcgcggtcc atctctataa tcagaggcac gacgagcacg aggaaggtgg    120
tgccggcaat ccacgcggct tttccggtgc tcttcaggag cttcttttgcg acgtaggcgg    180 tatcaaaagc cgctttcttg ccgcggtaca cgatgggtga ctgggaaacg gaggtggaaa    240
cacgggacag gattccgtcg tccgacgacg ctccgcctcc tctagtagac attctggtga    300
a                                                                   301
```

<210> SEQ ID NO 4
<211> LENGTH: 301
<212> TYPE: DNA
<213> ORGANISM: Sesamum indicum

<400> SEQUENCE: 4

```
gccattgatt taccaaaagc accaacccat tttggtgaga taattgggaa acttgttttg    60
gctggagcct tggacttcaa caaggtggca agggatattc tggcaaaagt aggtgacgac    120
tattaccaaa aggccatatt tactgctgct ctgaaggttg tcagctctga tccttcagga    180
aaggcattgc tcgattcaca ggcgtctgat gtcgctgcct gcgagagttt attttagagc    240
tcactccttg ttatgggaat tactggaaac atttgtaacc tcatagaaga aatgtgctat    300
t                                                                   301
```

<210> SEQ ID NO 5
<211> LENGTH: 301
<212> TYPE: DNA
<213> ORGANISM: Sesamum indicum

<400> SEQUENCE: 5

```
aatagaaaat tggtaattca aaagggaaag atggaaaaat gattaccatc cctgtcttca    60
gctgcctcaa cattcacaga atccttcgca agcacatctg tctctgtgga tgctttactt    120
```

| | |
|---|---:|
| tttattaccg gaaactgaac attgtgccgt ccattttccc taaaaagcat ataatctctc | 180 |
| tttgacagtg ttttcattac aagagttcct gcatttccat cattctaaga aagagaggtt | 240 |
| gattaaggca tccagcatcg cataaacata accaggaaaa tcgggagcaa acatagtact | 300 |
| g | 301 |

<210> SEQ ID NO 6
<211> LENGTH: 301
<212> TYPE: DNA
<213> ORGANISM: Sesamum indicum

<400> SEQUENCE: 6

| | |
|---|---:|
| ggaggcaaaa gaatacgggt tggttgatgc agtgatcgat gatggcaagc ctggactagt | 60 |
| cgcacccatc gcagatactg cacccccacc aaaaacccgt gtctgggatc tttggaaaat | 120 |
| cgaaggcagt aaaaaagcca agaaaaactt gccctccgaa gagaaactat tacaaaatgg | 180 |
| atacacagtt ggccaaggtg aagatgacag aagcacggaa caggtagagg aagcaccaac | 240 |
| atctcaatga gtaatgaatg ttgagatatt tcttgtatac actgtcaaac attgtagcta | 300 |
| g | 301 |

<210> SEQ ID NO 7
<211> LENGTH: 301
<212> TYPE: DNA
<213> ORGANISM: Sesamum indicum

<400> SEQUENCE: 7

| | |
|---|---:|
| agttgataaa ctgttgacta atcaaataat acgcattctg cacgcactca caaatactat | 60 |
| gattgttgtt tactgaataa ggttttcatg gaattttcac aggttaaatt ctagtaatca | 120 |
| cataaaagta tgtcgccagc tgactcttca tgcgaggaaa atgtgtacat ggccaagttg | 180 |
| gccgaacagg ctgagaggta tgaggagatg gttgaattca tggagaaggt tgtgaaggcc | 240 |
| gtggacactg atgagctgac agtcgaggaa aggaaccttc tctctgtggc atacaagaat | 300 |
| g | 301 |

<210> SEQ ID NO 8
<211> LENGTH: 301
<212> TYPE: DNA
<213> ORGANISM: Sesamum indicum

<400> SEQUENCE: 8

| | |
|---|---:|
| acgtaaatgt ttggatttaa tgtaatttaa tctaatgata ttgcaaatga gtaaattact | 60 |
| cccaaattat tcggataaag caatttaact tttggtttct tgtgagataa cattgcatgt | 120 |
| cctttatgaa ccaagagcag tggccgaggg actggtggtg gtaccgttgc caaggatgca | 180 |
| ttaggcaatg atgttattgc agcggaatgg ctcaaaaacc atggacctgg cgatcggaca | 240 |
| cttacacagg ggctgaaggt aattattgat ctagttgcaa aatagatcac ttattggctt | 300 |
| t | 301 |

<210> SEQ ID NO 9
<211> LENGTH: 301
<212> TYPE: DNA
<213> ORGANISM: Sesamum indicum

<400> SEQUENCE: 9

| | |
|---|---:|
| cctttagcag ggcatcactc tcttcaacat cgtactgcac cgagaggaat ttcgaagtga | 60 |
| gaaaaacttg gggctccgac acttcccctt tgctgtcgtt ttgaaaagtg agcttcaatt | 120 |

```
tcgccaaatt atccaacaat ttgcacgaga tttattaaa gaacacggag ctctcgctgt      180
cgaactccga cgtaactcgc agcttcggcc gacccatttg gaagagcccc agaaaaccgc     240
cgcctttcga accgccgtcg tccacggcgg gggatggtgg tggagacaga taatagggtt    300
g                                                                    301
```

<210> SEQ ID NO 10
<211> LENGTH: 301
<212> TYPE: DNA
<213> ORGANISM: Sesamum indicum

<400> SEQUENCE: 10

```
ccgggccaca actgatgctt attgtgttgc caaatatggt cagaagtggg tcaggacaag      60
gacaatcatc gacagttttg ctcctaaatg gaatgagcag tatacttggg aagtttttga    120
tccttgcact gttgtcacca ttggtgtatt tgataattgt catctgcaag gtggagataa    180
agctggaagg gattcaagaa ttgggaaggt aagaattcgc cttttcaactc tggaaacaga   240 ccgtgtgtac actcattctt atcctcttct agttttgcat ccttccgggg taaaaaagat    300
g                                                                    301
```

<210> SEQ ID NO 11
<211> LENGTH: 301
<212> TYPE: DNA
<213> ORGANISM: Sesamum indicum

<400> SEQUENCE: 11

```
ttagggcgtc gaattacttg gacgcgccga gcaagctagc ctgctgcaac tcaagctcgt      60
tgagctgctg ctcgcggtcc atctctataa tcagaggcac gacgagcacg aggaaggtgg    120
tgccggcaat ccacgcggct tttccggtgc ccttcaggag cttctttgcg acgtaggcgg    180
tatcaaaagc cgctttcttg ccgcggtaca cgatgggtga ctgggaaacg gaggtggaaa    240
cacgggacag gattccgtcg tccgacgacg ctccgcctcc tctagtagac attctggtga    300
a                                                                    301
```

<210> SEQ ID NO 12
<211> LENGTH: 301
<212> TYPE: DNA
<213> ORGANISM: Sesamum indicum

<400> SEQUENCE: 12

```
gccattgatt taccaaaagc accaacccat tttggtgaga taattgggaa acttgttttg      60
gctggagcct tggacttcaa caaggtggca agggatattc tggcaaaagt aggtgacgac    120
tattaccaaa aggccatatt tactgctgct gtgaaggttg tcagctctga tccttcagga    180
aaggcattgc tcgattcaca ggcgtctgat gtcgctgcct gcgagagttt attttagagc    240
tcactccttg ttatgggaat tactggaaac atttgtaacc tcatagaaga aatgtgctat    300
t                                                                    301
```

<210> SEQ ID NO 13
<211> LENGTH: 301
<212> TYPE: DNA
<213> ORGANISM: Sesamum indicum

<400> SEQUENCE: 13

```
aatagaaaat tggtaattca aaagggaaag atggaaaaat gattaccatc cctgtcttca      60
```

| | |
|---|---|
| gctgcctcaa cattcacaga atccttcgca agcacatctg tctctgtgga tgctttactt | 120 |
| tttattaccg gaaactgaac attgtgccgt gcattttcc taaaaagcat ataatctctc | 180 |
| tttgacagtg ttttcattac aagagttcct gcatttccat cattctaaga aagagaggtt | 240 |
| gattaaggca tccagcatcg cataaacata accaggaaaa tcgggagcaa acatagtact | 300 |
| g | 301 |

<210> SEQ ID NO 14
<211> LENGTH: 301
<212> TYPE: DNA
<213> ORGANISM: Sesamum indicum

<400> SEQUENCE: 14

| | |
|---|---|
| ggaggcaaaa gaatacgggt tggttgatgc agtgatcgat gatggcaagc ctggactagt | 60 |
| cgcacccatc gcagatactg caccccacc aaaaacccgt gtctgggatc tttggaaaat | 120 |
| cgaaggcagt aaaaaagcca agaaaaactt accctccgaa gagaaactat acaaaatgg | 180 |
| atacacagtt ggccaaggtg aagatgacag aagcacggaa caggtagagg aagcaccaac | 240 |
| atctcaatga gtaatgaatg ttgagatatt tcttgtatac actgtcaaac attgtagcta | 300 |
| g | 301 |

<210> SEQ ID NO 15
<211> LENGTH: 301
<212> TYPE: DNA
<213> ORGANISM: Sesamum indicum

<400> SEQUENCE: 15

| | |
|---|---|
| agttgataaa ctgttgacta atcaaataat acgcattctg cacgcactca caaatactat | 60 |
| gattgttgtt tactgaataa ggttttcatg gaattttcac aggttaaatt ctagtaatca | 120 |
| cataaaagta tgtcgccagc tgactcttca cgcgaggaaa atgtgtacat ggccaagttg | 180 |
| gccgaacagg ctgagaggta tgaggagatg gttgaattca tggagaaggt tgtgaaggcc | 240 |
| gtggacactg atgagctgac agtcgaggaa aggaaccttc tctctgtggc atacaagaat | 300 |
| g | 301 |

<210> SEQ ID NO 16
<211> LENGTH: 301
<212> TYPE: DNA
<213> ORGANISM: Sesamum indicum

<400> SEQUENCE: 16

| | |
|---|---|
| acgtaaatgt ttggatttaa tgtaatttaa tctaatgata ttgcaaatga gtaaattact | 60 |
| cccaaattat tcggataaag caatttaact tttggtttct tgtgagataa cattgcatgt | 120 |
| cctttatgaa ccaagagcag tggccgaggg gctggtggtg gtaccgttgc caaggatgca | 180 |
| ttaggcaatg atgttattgc agcggaatgg ctcaaaaacc atggacctgg cgatcggaca | 240 |
| cttacacagg ggctgaaggt aattattgat ctagttgcaa aatagatcac ttattggctt | 300 |
| t | 301 |

What is claimed is:

1. A sesame plant, progeny thereof or part thereof having shatter-resistant capsules, the sesame plant, progeny thereof or part thereof comprising at least three shatter-resistant capsule loci, wherein at least one shatter-resistant capsule locus is from at least one different sesame variety, wherein the at least three shatter-resistant capsule loci are associated with at least three quantitative trait loci (QTL) selected from QTL 1, QTL 2, QTL 3, QTL 4, QTL5, QTL 6 and QTL 7, wherein each of QTLs 1-7 is linked to at least one nucleic acid genetic marker that is associated with shatter resistance of the capsules, wherein the at least three QTLs comprise at least three of:

QTL 1 linked to genetic marker LG3_19205572, wherein LG3_19205572 has the nucleic acid sequence set forth in SEQ ID NO: 1 or 9, wherein QTL 1 is homozygous or heterozygous with respect to SEQ ID NO: 1, QTL 2 linked to genetic marker LG5_12832234, wherein LG5_12832234 has the nucleic acid sequence set forth in SEQ ID NO: 2 or 10, wherein QTL 2 is homozygous or heterozygous with respect to SEQ ID NO: 2, QTL 3 linked to genetic marker LG6_2739268, wherein LG6_2739268 has the nucleic acid sequence set forth in SEQ ID NO: 3 or 11, wherein QTL 3 is homozygous or heterozygous with respect to SEQ ID NO: 3, QTL 4 linked to genetic marker LG7_5141423, wherein LG7_5141423 has the nucleic acid sequence set forth in SEQ ID NO: 4 or 12, wherein QTL 4 is homozygous or heterozygous with respect to SEQ ID NO: 4, QTL 5 linked to genetic marker LG11_8864255, wherein LG11_8864255 has the nucleic acid sequence set forth in SEQ ID NO: 5 or 13, wherein QTL 5 is homozygous or heterozygous with respect to SEQ ID NO: 5, QTL 6 linked to genetic markers LG15_4900868 and LG15_5315334, wherein LG15_4900868 has the nucleic acid sequence set forth in SEQ ID NO: 6 or 14 and LG15_5315334 has the nucleic acid sequence set forth in SEQ ID NO: 7 or 15, wherein QTL 6 is homozygous or heterozygous with respect to SEQ ID NO: 6 and is homozygous or heterozygous with respect to SEQ ID NO: 7, and QTL 7 linked to genetic marker LG16_1563304, wherein LG16_1563304 has the nucleic acid sequence set forth in SEQ ID NO: 8 or 16, wherein QTL 7 is homozygous or heterozygous with respect to SEQ ID NO: 8, wherein the genetic markers are arranged in one or more marker cassettes, wherein:

marker cassette 1 comprises LG3_19205572, LG7_5141423 and LG15_5315334, wherein the alleles for said LG3_19205572, LG7_5141423 and LG15_5315334 are homozygous or heterozygous, marker cassette 2 comprises LG3_19205572, LG11_8864255 and LG15_5315334, wherein the alleles for said LG3_19205572, LG11_8864255 and LG15_5315334 are homozygous or heterozygous, marker cassette 3 comprises LG3_19205572, LG5_12832234, LG15_4900868 and LG15_5315334, wherein the alleles for said LG3_19205572, LG5_12832234, LG15_4900868 and LG15_5315334 are homozygous or heterozygous, and marker cassette 4 comprises LG6_2739268, LG11_8864255 and LG16_1563304, wherein the alleles for said LG6_2739268, LG11_8864255 and LG16_1563304 are homozygous or heterozygous.

2. The sesame plant, progeny thereof or part thereof having shatter-resistant capsules according to claim 1, wherein the shatter-resistant capsules are fully or partly shatter-resistant capsules, wherein shatter-resistant capsules are measured in fully developed capsules having at most 10% seed moisture, and wherein the shatter-resistant capsules have at least one of:

at least 80% seed retention after shaking the plant, at least 80% seed retention after the capsules are turned upside down, a ratio of at least 5:1 between a total length of the capsule and a length of a zone in which the capsule tips are open, or 20-30% of the capsules retain 90-95% of the seeds in fully developed green capsules before drying.

3. The sesame plant, progeny thereof or part thereof having shatter-resistant capsules according to claim 1, wherein the part thereof is any of: a seed, an endosperm, an ovule, pollen, cell, cell culture, tissue culture, plant organ, protoplast, meristem, embryo, or a combination thereof.

4. The sesame plant, progeny thereof or part thereof having shatter-resistant capsules according to claim 1, wherein the at least three QTLs comprises QTL 5 and at least another two of QTLs 1-4, 6 or 7.

5. The sesame plant, progeny thereof or part thereof having shatter-resistant capsules according to claim 1, wherein the at least three QTLs comprises QTL 1 and at least another two of QTLs 2-7.

6. The sesame plant, progeny thereof or part thereof having shatter-resistant capsules according to claim 1, wherein the at least three QTLs comprises QTLs 1, 4 and at least a part of QTL 6 having the nucleic acid sequence set forth in SEQ ID NO: 7 or 15.

7. The sesame plant, progeny thereof or part thereof having shatter-resistant capsules according to claim 1, wherein the at least three QTLs comprises QTLs 1, 5 and at least a part of QTL 6 having the nucleic acid sequence set forth in SEQ ID NO: 7 or 15.

8. The sesame plant, progeny thereof or part thereof having shatter-resistant capsules according to claim 1, wherein the at least three QTLs comprises QTLs 1, 2 and 6.

9. The sesame plant, progeny thereof or part thereof having shatter-resistant capsules according to claim 1, wherein the at least three QTLs comprises QTLs 3, 5 and 7.

10. A sesame plant, progeny thereof or part thereof having shatter-resistant capsules, the sesame plant, progeny thereof or part thereof comprising three shatter-resistant capsule loci, wherein at least one shatter-resistant capsule locus is from at least one different sesame variety, wherein each of the three shatter-resistant capsule loci is associated with a quantitative trait loci (QTL), wherein the QTLs are QTL 1, QTL 4 and QTL 6, and each QTL is linked to at least one nucleic acid genetic marker that is associated with shatter resistance of the capsules, wherein each nucleic acid genetic marker is arranged in a marker cassette 1 comprising:

QTL 1 linked to genetic marker LG3_19205572, wherein LG3_19205572 has the nucleic acid sequence set forth in SEQ ID NO: 1 or 9;

QTL 4 linked to genetic marker LG7_5141423, wherein LG7_5141423 has the nucleic acid sequence set forth in SEQ ID NO: 4 or 12; and QTL 6 linked to genetic marker LG15_5315334, wherein LG15_5315334 has the nucleic acid sequence set forth in SEQ ID NO: 7 or 15, wherein alleles for said LG3_19205572, LG7_5141423, and LG15_5315334 are homozygous or heterozygous.

11. A sesame plant, progeny thereof or part thereof having shatter-resistant capsules, the sesame plant, progeny thereof or part thereof comprising three shatter-resistant capsule loci, wherein at least one shatter-resistant capsule locus is from at least one different sesame variety, wherein at each of the three shatter-resistant capsule loci is associated with a quantitative trait loci (QTL), wherein the QTLs are QTL 1, QTL 2, and QTL 6, and each QTL is linked to at least one nucleic acid genetic marker that is associated with shatter resistance of the capsules, wherein each nucleic acid genetic marker is arranged in a marker cassette 3 comprising:

QTL 1 linked to genetic marker LG3_19205572, wherein LG3_19205572 has the nucleic acid sequence set forth in SEQ ID NO: 1 or 9;

QTL 2 linked to genetic marker LG5_12832234, wherein LG5_12832234 has the nucleic acid sequence set forth in SEQ ID NO: 2 or 10, QTL 6 linked to genetic markers LG15_4900868 and LG15_5315334, wherein LG15_4900868 has the nucleic acid sequence set forth in SEQ ID. NO: 6 or 14 and LG15_5315334 has the nucleic acid sequence set forth in SEQ ID NO: 7 or 15, wherein alleles for said LG3_19205572, LG5_12832234, LG15_4900868 and LG15_5315334 are homozygous or heterozygous.

12. The sesame plant, progeny thereof or part thereof having shatter-resistant capsules according to claim 1 comprising at least three of QTLs 1-7, wherein:
QTL 1 is homozygous with respect to SEQ ID NO: 1,
QTL 2 is homozygous with respect to SEQ ID NO: 2,
QTL 3 is homozygous with respect to SEQ ID NO: 3,
QTL 4 is homozygous with respect to SEQ ID NO: 4,
QTL 5 is homozygous with respect to SEQ ID NO: 5,
QTL 6 is homozygous with respect to SEQ ID NO: 6,
QTL 6 is homozygous with respect to SEQ ID NO: 7, and
QTL 7 is homozygous with respect to SEQ ID NO: 8.

13. The sesame plant, progeny thereof or part thereof having shatter-resistant capsules according to claim 12 comprising QTL 1, QTL 4 and QTL 6, wherein:
QTL 1 is homozygous with respect to SEQ ID NO: 1,
QTL 4 is homozygous with respect to SEQ ID NO: 4, and
QTL 6 is homozygous with respect to SEQ ID NO: 7.

14. The sesame plant, progeny thereof or part thereof having shatter-resistant capsules according to claim 12 comprising QTL1, QTL 5 and QTL 6, wherein:
QTL 1 is homozygous with respect to SEQ ID NO: 1,
QTL 5 is homozygous with respect to SEQ ID NO: 5, and
QTL 6 is homozygous with respect to SEQ ID NO: 7.

15. The sesame plant, progeny thereof or part thereof having shatter-resistant capsules according to claim 12 comprising QTL1, QTL 2 and QTL 6, wherein:
QTL 1 is homozygous with respect to SEQ ID NO: 1,
QTL 2 is homozygous with respect to SEQ ID NO: 2,
QTL 6 is homozygous with respect to SEQ ID NO: 6, and
QTL 6 is homozygous with respect to SEQ ID NO: 7.

16. The sesame plant, progeny thereof or part thereof having shatter-resistant capsules according to claim 12 comprising QTL 3, QTL 5 and QTL 7 wherein:
QTL 3 is homozygous with respect to SEQ ID NO: 3,
QTL 5 is homozygous with respect to SEQ ID NO: 5, and
QTL 7 is homozygous with respect to SEQ ID NO: 8.

17. The sesame plant, progeny thereof or part thereof having shatter-resistant capsules, according to claim 12, comprising:
QTL 1 is homozygous with respect to SEQ ID NO: 1,
QTL 2 is homozygous with respect to SEQ ID NO: 2,
QTL 3 is homozygous with respect to SEQ ID NO: 3,
QTL 4 is homozygous with respect to SEQ ID NO: 4,
QTL 5 is homozygous with respect to SEQ ID NO: 5,
QTL 6 is homozygous with respect to SEQ ID NO: 6,
QTL 6 is homozygous with respect to SEQ ID NO: 7, and
QTL 7 is homozygous with respect to SEQ ID NO: 8;
wherein the genetic markers are arranged in four marker cassettes, wherein:
marker cassette 1 comprises LG3_19205572, LG7_5141423 and LG15_5315334,
marker cassette 2 comprises LG3_19205572, LG11_8864255 and LG15_5315334,
marker cassette 3 comprises LG3_19205572, LG5_12832234, LG15_4900868 and LG15_5315334, and
marker cassette 4 comprises LG6_2739268, LG11_8864255 and LG16_1563304.

* * * * *